US006998245B1

(12) United States Patent
Uemura et al.

(10) Patent No.: US 6,998,245 B1
(45) Date of Patent: Feb. 14, 2006

(54) SERINE PROTEASE BSSP5

(75) Inventors: Hidetoshi Uemura, Hyogo (JP); Akira Okui, Nara (JP); Katsuya Kominami, Osaka (JP); Nozomi Yamaguchi, Kyoto (JP); Shinichi Mitsui, Kyoto (JP)

(73) Assignee: FUSO Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/856,319

(22) PCT Filed: Nov. 19, 1999

(86) PCT No.: PCT/JP99/06473

§ 371 (c)(1),
(2), (4) Date: May 21, 2001

(87) PCT Pub. No.: WO00/31243

PCT Pub. Date: Jun. 2, 2000

(30) Foreign Application Priority Data

Nov. 20, 1998  (JP) .............................. 1998/347806

(51) Int. Cl.
G01N 33/53  (2006.01)
G01N 33/573  (2006.01)
C07K 16/18  (2006.01)

(52) U.S. Cl. ...................... 435/7.4; 435/7.1; 530/387.1
(58) Field of Classification Search ............. 530/387.1, 530/7.1, 7.4; 435/7.1, 7.4
See application file for complete search history.

(56) References Cited

U.S. PATENT DOCUMENTS 4,446,122 A * 5/1984 Chu et al.
5,731,439 A 3/1998 Carini et al.

FOREIGN PATENT DOCUMENTS

WO   WO 97/24135    7/1997
WO   WO 9/54446 A2  10/1999

OTHER PUBLICATIONS

Carrere et al. Human pancreatic chymotrypsinogen A: a non-competitive enzyme immunoassay, and molecular forms in serum and amniotic fluid. Biochim Biophys Acta. Aug. 6, 1986;883(1):46-53.*

Geokas et al. Immunoreactive forms of human pancreatic chymotrypsin in normal plasma. J Biol Chem. Apr. 25, 1979;254(8):2775-81.*

Lesi et al. Digestion 1984 30:114-115.*

Iwaki et al. Radioimmunoassay for human pancreatic chymotrypsin and measurement of serum immunoreactive chymotrypsin contents in various diseases. Res Commun Chem Pathol Pharmacol. Jun. 1983;40(3):489-96.*

"Chapter 6: Monoclonal Antibodies" Antibodies: a laboratory manual (Harlow and Lane eds.), Cold Spring Harbor Laboratory, 188, pp. 139-149.*

Frank Larsen et al; "A Tight Cluster of Five Unrelated Human Genes on Chromosome 16q22.1"; *Human Molecular Genetics*, vol. 2, No. 10, pp. 1589-1595 (1993).

Yoshiro Yamamura et al; "Molecular Cloning of a Novel Brain-Specific Serine Protease with a Kringle-like Structure and Three Scavenger Receptor Cysteine-Rich Motifs"; *Biochemical and Biophysical Research Communications*, Article No. RC977417, pp. 239, 386-392 (1997).

Database EMBL Online!, Larsen et al; *H. sapiens mRNA for chymotrypsin*. Oct. 13, 1993; Database accession No. X71877; XP-002201987.

Database EMBL Online!, Larsen et al; *Chymotrypsin-like protease CTRL-1 precursor*. Feb. 1, 1995, Database accession No. P40313; XP002201988.

Reseland et al., A novel human chymotrypsin-like digestive enzyme, *The Journal of Biological Chemistry*, 272:(12) 8099-8104 (1997).

* cited by examiner

*Primary Examiner*—David Guzo
*Assistant Examiner*—Daniel M. Sullivan
(74) *Attorney, Agent, or Firm*—Browdy and Neimark, PLLC

(57) ABSTRACT

There are provided proteins having the amino acid sequences represented by SEQ ID NOS: 2 and 4; proteins having amino acid sequences derived from these amino acid sequences by deletion, substitution or addition of one to several amino acids; and nucleotide sequences encoding the same; transgenic non-human animals with altered expression level of a serine protease BSSP5; an antibody against BSSP5; and a method for detecting BSSP5 in a specimen by using the antibody. The BSSP5 provied by the present invention can be used for treating and diagnosing various diseases such as Alzheimer's disease (AD), epilepsy, cancer, inflammation, sterility and prostatic hypertropy and detecting pancreatitis in various tissues including brain, prostate gland, placenta, pancreas and spleen.

1 Claim, 6 Drawing Sheets

0, 6, 18, 24 hours

SERINE PROTEASE BSSP5

The present application is the national stage under 35 U.S.C. §371 of international application PCT/JP99/06473, filed 19 Nov. 1999 which designated the United States, and which application was not published in the English language.

FIELD OF THE INVENTION

The present invention relates to isolated polynucleotides of human and mouse serine proteases (hereinafter referred to as "hBSSP5" and "mBSSP5", respectively, and, in case no differentiation thereof from each other is needed, simply referred to as "BSSP5"), and their homologous forms, mature forms, precursors and polymorphic variants as well as a method for detecting thereof. Further, it relates to hBSSP5 and mBSSP5 proteins, compositions containing hBSSP5 and mBSSP5 polynucleotides and proteins, as well as their production and use.

BACKGROUND OF THE INVENTION

In general, proteases are biosynthesized as inactive precursors. They undergo limited hydrolysis in molecules to convert into activated type proteases. In so far as enzymes are proteases, they have an activity for hydrolyzing a peptide bond, while their action modes are varied according to kinds of proteases. According to a particular kind of catalytic site, proteases are divided into serine proteases, cysteine proteases, aspartate proteases, metal proteases and the like. Proteases of each kind have a variety of properties, ranging from a protease having general digestive properties to a protease having various regulatory domains and strict substrate specificity, thereby specifically hydrolyzing only characteristic proteins.

Further, proteins undergo various processing even after translation to produce active proteins. In many secretory proteins, a protein are first synthesized on the ribosome in cytoplasm as an inactive precursor (pro-form) which comprises an active protein bearing at the N-terminus thereof a peptide of about 15 to 60 amino acids responsible for secretion (secretory signal). This peptide region is concerned with the mechanism for passing through the cell membrane and is removed upon cleavage by a specific protease during the passage through the membrane, in almost all the cases, to produce the mature type protein. A secretory signal has a broad hydrophobic region comprising hydrophobic amino acids in the middle of the sequence, and basic amino acid residues at a site close to the N-terminus. A secretory signal is a synonym of a signal peptide. In addition, in some proteins, a peptide moiety which functions as a secretory signal is further attached to the N-terminus of the inactive precursor. Such a protein is called a preproprotein (prepro-form).

For example, trypsin is present as a prepro-form immediately after translation into amino acids. After being secreted from cells, it is present as a pro-form and is converted into active trypsin in duodenum upon limited hydrolysis by enteropeptidase or by trypsin itself.

The optimal pH range of serine proteases is neutral to weak alkaline and, in general, many of them have a molecular weight of about 30,000 or lower. All proteases of blood coagulation, fibrinolysis and complement systems having a large molecular weight belong to trypsin-like serine proteases. They have many regulator domains and form a protease cascade which is of very importance to reactions in a living body.

Recently, cDNAs and amino acid sequences of many novel proteases have been determined by PCR for consensus sequences of serine proteases using oligonucleotide primers. According to this method, novel proteases have been found by various researchers such as Yamamura et al. (Yamanura, Y et al., Biochem. Biophys. Res. Commun., 239, 386, 1997), Gschwend, et al. (Gschwend, T. P. et al., Mol. Cell. Neurosci., 9. 207, 1997), Chen et al. (Chen, Z-L, et al., J. Neurosci., 15, 5088, 1995) and others.

SEQ ID NO: 3 of JP 9-149790 A discloses neurosin as a novel serine protease. Neurosin has also been reported in Biochimica et Byophysica Acta, 1350, 11–14, 1997. By this, there is provided a method for mass production of neurosin using the serine protease gene and a method for screening specific inhibitors using the enzyme. In addition, the screening method has been shown to be useful for screening medicines for treating various diseases.

Serine proteases expressed in a brain-nerve system such as neurosin are considered to play various roles in the brain-nerve system. Therefore, there is a possibility that isolation of a gene encoding a novel protease expressed in a brain-nerve system and production of a protein using the gene would be useful for diagnosis or treatment of various diseases related to the brain-nerve system.

Nowadays, in general, clinical diagnosis of Alzheimer's disease is conducted based on the diagnosis standard of DSM-IIIR and NINCDS-ADRDA (Mckhann, G. et al., Neurology, 34. 939, 1994) or the diagnosis standard of DSM-IV (American Psychiatric Association; Diagnostic and statistical manuals of mental disorders, 4th ed., Washington D.C., American Psychiatric Association, 1994). However, these standards are conditioned by decline of recognition functions which causes a severe disability in a daily life or a social life. Then, it is pointed out that the diagnosis is less scientific objectivity because the diagnosis may be influenced by the level of an individual's social life and further the specialty and experience of a physician who diagnoses particular conditions. In addition, definite diagnosis of Alzheimer's disease is conducted by pathohistological analyses and, in this respect, substantial inconsistency between clinical diagnosis and autopsy diagnosis is pointed out.

At present, image diagnosis is employed as a supplemental means in clinical diagnosis of Alzheimer's diagnosis and it is possible to analyze brain functions, for example, decline of metabolism and atrophy in specific sites such as hippocampus, parietal lobe of cerebral cortex and the like which are specific for Alzheimer's disease by PET and SPECT. However, to define Alzheimer's disease based on lowering of a blood flow from parietal lobe to temporal lobe is very dangerous. In addition, there is few report showing that MRS testicle useful for patients with dementia including those of Alzheimer's disease. Further, although CT-MRI image diagnosis is used, a lesion of white matter such as atrophy of brain, PVL or the like is not specific for Alzheimer type dementia. Since it has been reported that atrophy of brain proceeds as getting older, the above observation is not necessarily found in Alzheimer type dementia. Furthermore, since an image obtained by MRI varies according to strength of a magnetic field, performance of an apparatus and imaging conditions, numerical data obtain in different facilities cannot be compared with each other except atrophic change. In addition, there is a limit to image measurement. Further, enlargement of ventricle can be recognized in vascular dementia cases and there are cases wherein atrophy of hippocampus is observed after ischemia of basilar artery.

Under these circumstances, many researchers have requested to develop biological diagnosis markers as a means for providing better precision and objectivity for clinical diagnosis of Alzheimer's disease. At the same time, the following important roles in the future will be expected.

1) Objective judgment system of effect of medicaments for treating Alzheimer's disease.
2) Detection of Alzheimer's disease before a diagnosis standard is met, or disease conditions are manifested.

Further, data obtained in different facilities can be compared with each other by using the same diagnosis marker. Therefore, development of biological diagnosis markers is recognized to be a most important field among fields of Alzheimer's disease studies and its future prospects will be expected. Approaches to development of biological diagnosis markers up to now are divided into that based on constitute components of characteristic pathological changes of Alzheimer's disease such as senile plaque and neurofibril change, and an approach based on other measures. Examples of the former include cerebrospinal fluid tau protein, Aβ and its precursor, βAPP. Examples of the latter include mydriasis test with cholilytic drug, Apo E and other genes relating to Alzheimer's disease. However, no good results are obtained.

Serine proteases are also considered to play important role in cancer cells. The reason why extermination of cancer by surgical treatment or topical irradiation of radioactive ray is difficult is metastasis capability of cancer. For spread of solid tumor cells in a body, they should loosen their adhesion to original adjacent cells, followed by separating from an original tissue, passing through other tissues to reach blood vessel or lymph node, entering into the circulatory system through stratum basal and endothelial layer of the vessel, leave from the circulatory system at somewhere in the body, and surviving and proliferating in a new environment. While adhesion to adjacent epidermal cells is lost when expression of cadherin which is an intercellular adhesive molecule of epithelium is stopped, to break through tissues is considered to depend on proteolytic enzymes which decompose an extracellular matrix.

As enzymes which decompose the matrix, mainly, metal proteases (Rha, S. Y. et al., Breast Cancer Research Treatment, 43, 175, 1997) and serine proteases are known. They cooperate to decompose matrix protein such as collagen, laminin and fibronectin. Among serine proteases known to be concerned in decomposition of the matrix, in particular, there is urokinase type plasminogen activator (U-PA). U-PA has a role as a trigger specific for a protein decomposition chain reaction. Its direct target is plasminogen. It is present in blood abundantly and is a precursor of an inactive serine protease which accumulates in reconstructed sites of tissues such as injured sites and tumors as well as inflammatory sites. In addition, as proteases which are concerned in metastasis and infiltration of cancers, for example, a tissue factor, lysosomal type hydrolase and collagenase have been known.

At present, cancer is the top cause of death in Japan and more than 200,000 people are died per year. Then, specific substances which can be used as markers for diagnosis and therapy or prophylaxis of cancer are studied intensively. Such specific substances are referred to as tumor markers or tumor marker relating biomarkers. They are utilized in aid of diagnosis before treatment of cancer, for presuming carcinogenic organ and pathological tissue type, for monitoring effect of treatment, for finding recurrence early, for presuming prognosis, and the like. At present, tumor markers are essential in clinical analyses. Among them, alpha fetoprotein (AFP) which has high specificity to hepatocellular carcinoma and yolk sac tumor (Taketa K. et al., Tumour Biol., 9, 110, 1988), and carcinoembronic antigen (CEA) are used worldwide. In the future, tumor markers will be required more and more, and it is desired to develop, for example, organ specific markers and tumor cell specific markers which are highly reliable serologic diagnosis of cancer. Up to now, humunglandular kallikrein (hK2) which is a serine protease expressed at human prostatic epithelial cells has been reported as a marker for prostatic cancer. And, hK2 has 78% homology with the sequence of prostatic specific antigen (PSA) and PSA is also used widely as a biochemical marker of prostatic cancer (Mikolajczyk, S. d. et al., Prostate, 34, 44, 1998; Pannek, J. et al., Oncology, 11, 1273, 1997; Chu, T. M. et al., Tumour Biology, 18, 123, 1997; Hsieh, M. et al., Cancer Res., 57, 2651, 1997).

OBJECTS OF THE INVENTION

Thus, the main object of the present invention is to provide a novel serine protease which can be used for treating or diagnosing various diseases such as Alzheimer's disease (AD), epilepsy, cancer, inflammation, sterility, prostate hypertropy and the like in various tissues such as brain, lung, prostate, testicle, skeletal muscle, liver and the like, and can be used as an excellent marker instead of that presently used.

SUMMARY OF THE INVENTION

Under these circumstances, the present inventors have succeeded in cloning of cDNA encoding novel human and mouse serine proteases.

In summary, the 1st feature of the present invention is amino acid sequences of biological active mature serine proteases hBSSP5 and MBSSP5 and nucleotide sequences encoding the amino acid sequences.

That is, they are the amino acid sequence composed of 231 amino acids (mature type hBSSP5 (the 1st to 231th amino acids of SEQ ID NO: 2)) and a nucleotide sequence encoding the amino acid sequence (the 110th to 802nd bases of SEQ ID NO: 1). In addition, they include amino acid sequences substantially similar to SEQ ID NO: 2 and nucleotide sequences encoding such similar amino acid sequences. Further, they include modified derivatives of proteins having these amino acid sequences. An amino acid sequence substantially similar to a given amino acid sequence used herein means an amino acid sequence derived from the given amino acid sequence by modification such as substitution, deletion, addition and/or insertion of one to several amino acids with maintaining the same property as that of the protein having the given amino acid sequence. The modified derivative of the proteins includes, for example, phosphate adduct, sugar chain adduct, metal adduct (e.g., calcium adduct), the protein fused to another protein such as albumin etc., dimer of the protein, and the like.

Further, they are the amino acid sequence composed of 231 amino acids (mature type mBSSP5 (the 1st to 231th amino acids of SEQ ID NO: 4)) and a nucleotide sequence encoding the amino acid sequence (the 132nd to 824th bases of SEQ ID NO: 3). In addition, they include amino acid sequences substantially similar to the anubi acid sequence and nucleotide sequences encoding such similar amino acid sequences. Further, they include modified derivatives of proteins having these amino acid sequences.

The 2nd feature of the present invention is an amino acid sequence composed of 33 amino acids represented by the −33rd to −1st amino acids represented by SEQ ID NO: 4 and a nucleotide sequence encoding the amino acid sequence (the 33rd to 131st bases of SEQ ID NO: 3). In addition, this feature includes amino acid sequences substantially similar to the amino acid sequence and nucleotide sequences encoding these substantially similar amino acid sequences. Further, this feature includes modified derivatives of proteins having these amino acid sequences.

The 3rd feature of the present invention is an amino acid sequence composed of 264 amino acids (precursor type mBSSP5 (the −33rd to 231st amino acids of SEQ ID NO: 4)) wherein 33 amino acids compsed of −33rd to −1st amino acids represented by SEQ ID NO: 4 are added to the N-terminus side of the mature type mBSSP5 amino acid sequence (SEQ ID NO: 4) and a nucleotide sequence encoding the amino acid sequence (the 33rd to 824th bases of SEQ ID NO: 3). In addition, this feature includes amino acid sequences substantially similar to the amino acid sequence represented by SEQ ID NO: 4 and nucleotide sequences encoding these substantially similar amino acid sequences. Further, this feature includes modified derivatives of proteins having there amino acid sequences.

The present invention also relates to the nucleotide sequences represented by SEQ ID NOS: 1 and 3 and nucleotide sequences similar to these sequences.

The 4th feature of the present invention is a vector comprising the nucleotide sequence according to any of the above 1st to the 3rd features, and transformant cells transformed with the vector.

The 5th feature of the present invention is a process for producing BSSP5 protein from the transformed cells of the 4th feature.

The 6th feature of the present invention is a transgenic non-human animal, wherein the expression level of BSSP5 gene has been altered.

The 7th feature of the present invention is an antibody against BSSP5 protein or its fragment and a process for producing thereof.

The 8th feature of the present invention is a method for determining BSSP5 protein or its fragment in a specimen using the antibody of the 7th feature.

The 9th feature of the present invention is a diagnostic marker of diseases comprising BSSP5 protein.

The 10th feature of the present invention is a method for detecting pancreatitis by determining concentration of BSSP5 protein, a pharmaceutical composition comprising an antibody against BSSP5 protein or its fragment, and use of BSSP5 protein for preparing an antibody for detecting pancreatitis.

Hereinafter, unless otherwise stated, the nucleotide sequence represented by each SEQ ID NO: includes the above-described various fragments thereof, and similar nucleotide sequences and their fragments. Likewise, the amino acid sequence represented by each SEQ ID NO: includes the above-described various fragments thereof, similar amino acid sequences and their fragments, and modified derivatives thereof. In addition, unless otherwise stated, BSSP5, hBSSP5, and mBSSP5 include proteins having the above-described respective amino acid sequences.

DETAILED DESCRIPTION OF THE INVENTION

Figure 1:
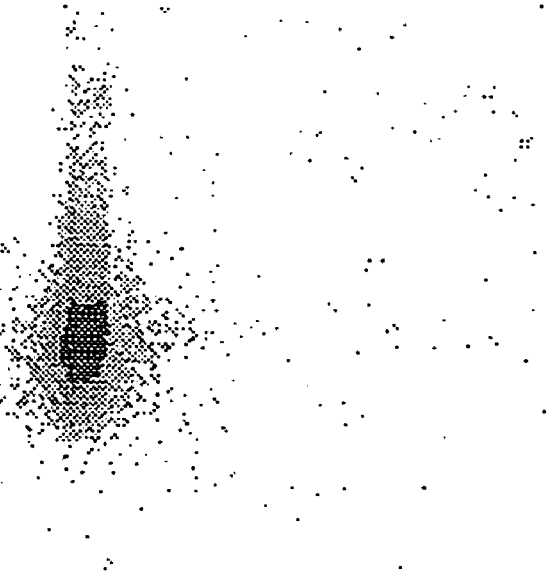
FIG. 1 illustrates the results of northern blotting using human multiple tissue blot membrane.

The nucleotide sequences encoding hBSSP5 or mBSSP5 of the present invention can be obtained by preparing mRNAs from cells expressing the protein and converting it into double stranded DNAs according to a conventional manner. For preparing mRNA, guanidine isothiocyanate-calcium chloride method (Chirwin, et al., Biochemistry, 18, 5294, 1979) or the like can be used. For preparing poly (A)+RNA from total RNAs, there can be used affinity chromatography using a carrier, for example, Sepharose, latex particles, etc., to which oligo (dT) is attached, and the like. The above-obtained RNA can be used as a template and treated with reverse transcriptase by using, as a primer, oligo (dT) which is complementary to the poly (A) strand at the 3'-terminus, or a random primer, or a synthesized oligonucleotide corresponding to a part of the amino acid sequence of hBSSP5 or mBSSP5 to obtain a hybrid mRNA strand comprising DNA complementary to the mRNA or cDNA. The double stranded DNA can be obtained by treating the above-obtained hybrid mRNA strand with *E. coli* RNase, *E. coli* DNA polymerase and *E. coli* DNA ligase to convert into a DNA strand.

It is also possible to carry out cloning by RT-PCR method using primers synthesized on the basis of the nucleotide sequence of hBSSP5 or mBSSP5 gene and using hBSSP5 or mBSSP5 expressing cell poly (A)+RNA as a template. Alternatively, the desired cDNA can be obtained without using PCR by preparing or synthesizing a probe on the basis of the nucleotide sequence of hBSSP5 or mBSSP5 gene and screening a cDNA library directly. Among genes obtained by these methods, the gene of the present invention can be selected by confirming a nucleotide sequence thereof. The gene of the present invention can also be prepared according to a conventional method using chemical syntheses of nucleic acids, for example, phosphoamidite method (Mattencci, M. D. et al., J. Am. Chem. Soc., 130, 3185, 1981) and the like.

By using the thus-obtained hBSSP5 or mBSSP5 gene, their expression in various tissues can be examined.

In case of northern blotting analysis, the expression of hBSSP5 is observed in pancreas and the expression of mBSSP5 is observed in spleen. In case of RT-PCR analysis, the expression of hBSSP5 is observed in brain of the fetuses and placenta of the adults, and mBSSP5 shows the expression in brain of newborn to grown-up mice and in testicle of grown-up mice. Then, the novel proteases of the present invention are presumed to play various roles in brain, placenta, testicle, pancreas and spleen. For example, in brain, there is a possibility that they can be used for treatment and diagnosis of brain diseases such as Alzheimer's disease (AD), epilepsy, brain tumor and the like. Further, in other tissues, there is a possibility that BSSP5 of the present invention and a gene encoding it can be used for treatment and diagnosis of various diseases such as cancer, inflammation, sterility, prostate hypertrophy and the like.

Further, it is presumed they may have a certain influence on blood coagulation, fibrinolysis and complement systems. Furthermore, there is a possibility that inhibitors of serine proteases can be used for treatment and prevention of Alzheimer's disease, epilepsy, cancer, inflammation, sterility, prostate hypertrophy and the like. Moreover, increase in a blood level of BSSP5 of the present invention is observed in a rat pancreatitis model and therefore it can be used for detection of pancreatitis.

The present inventors have shown that the mature type of novel human serine protease (hBSSP5) is composed of 231 amino acids, and the mature type of novel mouse serine protease (mBSSP5) is composed of 231 amino acids and its precursor type is composed of 264 amino acids. Further, the amino acid sequences of the mature type serine proteases contain consensus sequences having serine protease activity.

The term "pro part" used herein means a part of a pro-form, i.e., the pro-form from which the corresponding active type protein part is removed. The term "pre part" used herein means a part of a prepro-form, i.e., the prepro-form from which the corresponding pro-form is removed. The term "prepro part" used herein means a part of a prepro-form, i.e., the prepro-form from which the corresponding active type protein part is removed.

The amino acid sequence represented by the 1st to 231st amino acids of SEQ ID NO: 2 is the BSSP5 mature or active type protein composed of 231 amino acids, and the nucleotide sequence encoding the amino acid sequence represented by the 110th to 802nd bases of SEQ ID NO: 1 is composed of 693 bases. The present inventors have shown that the serine protease activity is maintained even when one to several amino acids of the N-terminus in the amino acid seqeunce of the mature type protein of hBSSP5 is deleted or added, while the sequence represented by the 1st to 231st amino acids of SEQ ID NO: 2 is preferred.

The amino acid sequence represented by SEQ ID NO: 4 is mBSSP5 protein composed of 264 amino acids, and the nucleotide sequence encoding the amino acid sequence represented SEQ ID NO: 3 is composed of 792 bases. The present inventors have shown that the serine protease activity is maintained even when one to several amino acids of the N-terminus in the amino acid sequence of the mature type protein of mBSSP5 is deleted or added, while the sequence reprsented by SEQ ID NO: 4 is preferred. The sequence of the −33th to −1st amino acids of SEQ ID NO: 4 is the prepro or pro part and the amino acid sequence represented by the −33rd to 231th of the amino acids is considered to be a precursor type of mBSSP5 protein.

In general, many genes of eucaryote exhibit polymorphism and, sometimes, one or more amino acids are substituted by this phenomenon. Further, even in such case, sometimes, a protein maintains its activity. Then, the present invention includes a gene encoding a protein obtained by modifying a gene encoding the amino acid sequence represented by SEQ ID NO: 2 or 4, artificially, in so far as the protein has the characteristic function of the gene of the present invention. Further, the present invention includes a protein which is a modification of the amino acid sequence represented by SEQ ID NO: 2 or 4 in so far as the protein has the characteristics of the present invention. Modification is understood to include substitution, deletion, addition and/or insertion. In particular, the present inventors have shown that, even when several amino acids are added to or deleted from the N-terminus amino acid of hBSSP5 or mBSSP5 mature protein represented by SEQ ID NO: 2 or 4, the resultant sequence maintains its activity.

That is, the present invention includes a protein comprising either amino acid sequence described in SEQ ID NOS: 2 and 4; or one of these amino acid sequences wherein one to several amino acids have been substituted, deleted, added and/or inserted, and being belonging to serine protease family.

Each codon for the desired amino acid itself has been known and it can be selected freely. For example, codons can be determined according to a conventional manner by taking into consideration of frequency of use of codons in a host to be utilized (Grantham, R. et al., Nucleic Acids Res., 9, r43, 1989). Therefore, the present invention also includes a nucleotide sequence appropriately modified by taking into consideration of degeneracy of a codon. Further, these nucleotide sequences can be modified by a site directed mutagenesis using a primer composed of a synthetic oligonucleotide encoding the desired modification (Mark, D. F. et al., Proc. Natl. Acad. Sci. USA., 81, 5662, 1984), or the like.

Furthermore, the DNA of the present invention includes DNA which is hybridizable to either of nucleotide sequences described in SEQ ID NOS: 1 and 3, or nucleotide sequences complementary to these nucleotide sequences in so far as the protein encoded by the nucleotide sequence has the same properties as those of hBSSP5 or mBSSP5 of the present invention. It is considered that many of sequences which are hybridizable to a given sequence under stringent conditions have a similar activity to that of a protein encoded by the given sequence. The stringent conditions according to the present invention includes, for example, incubation in a solution containing 5×SSC, 5% Denhardt's solution (0.1% BSA, 0.1% Ficol 1400, 0.1% PVP), 0.5% SDS and 20 $\mu$g/ml denatured salmon sperm DNA at 37° C. overnight, followed by washing with 2×SSC containing 0.1% SDS at room temperature. Instead of SSC, SSPE can be appropriately used.

Probes for detecting a hBSSP5 or mBSSP5 gene can be designed based on either of nucleotide sequences described in SEQ ID NOS: 1 and 3. Or, primers can be designed for amplifying DNA or RNA containing the nucleotide sequence. To design probes or primers is carried out routinely by a person skilled in the art. An oligonucleotide having a designed nucleotide sequence can be synthesized chemically. And, when a suitable label is added to the oligonucleotide, the resultant oligonucleotide can be utilized in various hybridization assays. Or, it can be utilized in nucleic acid synthesis reactions such as PCR. An oligonucleotide to be utilized as a primer has, preferably, at least 10 bases, more preferably 15 to 50 bases in length. An oligonucleotide to be utilized as a probe has, preferably, 100 bases to full length.

Moreover, it is possible to obtain a promoter region and an enhancer region of a hBSSP5 or mBSSP5 gene present in the genome based on the cDNA nucleotide sequence of hBSSP5 or mBSSP5 provided by the present invention. Specifically, these control regions can be obtained according to the same manner as described in JP 6-181767 A; J. Immunol., 155, 2477, 1995; Proc. Natl. Acad. Sci., USA, 92, 3561, 1995 and the like. The promoter region used herein means a DNA region which is present upstream from a transcription initiation site and controls expression of a gene. The enhancer region used herein means a DNA region which is present in an intron, a 5'-non-translated region or a 3'-non-translated region and enhances expression of a gene.

The present invention also relates to a vector comprising the nucleotide sequence represented by SEQ ID NO: 1 or a nucleotide sequence encoding the amino acid sequence represented by SEQ ID NO: 2; the nucleotide sequence represented by SEQ ID NO: 3 or a nucleotide sequence encoding the amino acid sequence represented by SEQ ID NO: 4; or a nucleotide sequence similar to them. A nucleotide sequence similar to a give nucleotide sequence used herein means a nucleotide sequence which is hybridizable to the given nucleotide sequence or its complementary nucleotide sequence under the above-described stringent conditions and encodes a protein having the same properties as those of the protein encoded by the nucleotide sequence.

The vector is not specifically limited in so far as it can express the protein of the present invention. Examples thereof include pBAD/His, pRSETA, pcDNA2.1, pTrcHis2A, pYES2, pBlueBac4.5, pcDNA3.1 and pSecTag2 manufacture by Invitrogen, pET and pBAC manufactured by Novagen, pGEM manufactured by Promega, pBluescriptII manufactured by Stratagene, pGEX and pUC18/19 manufactured by Pharmacia, PfastBAC1 manufactured by GIBCO and the like. Preferably, a protein expression vector (described in the specification of a patent application entitled "Protein expression vector and its use" and filed by the same applicant on the same day) is used. This expression vector is constructed by using pCRII-TOPO vector described in the Examples hereinafter, or a commercially available expression vector, for example pSecTag2A vector or pSecTag2B vector (Invitrogen) and integrating a secretory signal nucleotide sequence suitable for expression of the protein of the present invention, in the 3' downstream side thereof, a Tag nucleotide sequence, a cleavable nucleotide sequence and a cloning site, into which a nucleotide sequence encoding a target protein can be inserted, in this order. More specifically, it is preferred to use trypsin signal as the secretory signal, a nucleotide sequence encoding polyhistidine as the Tag nucleotide sequence, and a nucleotide sequence encoding an amino acid sequence which is susceptible to enzyme-specific cleavage, i.e., a nucleotide sequence encoding the amino acid sequence of Asp-Asp-Asp-Asp-Lys (SEQ ID NO:33) (said amino acid sequence is recognized by enterokinase, and the recombinant fusion protein is cleaved at the C-terminus part thereof) as the cleavable nucleotide sequence.

Furthermore, the present invention provides transformed cells having the nucleotide sequence of the present invention in an expressible state by means of the above vector. Preferably, host cells to be used for the transformed cells of the present invention are animal cells and insect cells. However, host cells include any cells (including those of microorganisms) which can express a nucleotide sequence encoding the desired protein in the expression vector of the present invention and can secrete extracellularly.

The animal cells and insect cells used herein include cells derived from human being and cells derived from fly or silk worm. For example, there are CHO cell, COS cell, BHK cell, Vero cell, myeloma cell, HEK293 cell, HeLa cell, Jurkat cell, mouse L cell, mouse C127 cell, mouse FM3A cell, mouse fibroblast, osteoblast, cartilage cell, S2, Sf9, Sf21, High Five™ (registered trade mark) cell and the like. The microorganisms used herein include *E. coli*, yeast or the like.

The protein of the present invention as such can be expressed as a recombinant fused protein so as to facilitate isolation, purification and recognition. The recombinant fused protein used herein means a protein expressed as an adduct wherein a suitable peptide chain are added to the N-terminus and/or C-terminus of the desired protein expressed by a nucleotide sequence encoding the desired protein. The recombinant protein used herein means that obtained by integrating a nucleotide sequence encoding the desired protein in the expression vector of the present invention and cut off an amino acid sequence which derived from nucleic acids other than those encoding the desired protein from the expressed recombinant fused protein, and is substantially the same as the protein of the present invention.

Introduction of the above vector into host cells can be carried out by, for example, transfection according to lipopolyamine method, DEAE-dextran method, Hanahan method, lipofectin method or calcium phosphate method, microinjection, eletroporation and the like.

As described above, the present invention also relates to a process for producing hBSSP5 or mBSSP5 comprising culturing cells transformed with the above nucleotide sequence of the present invention and collecting the produced hBSSP5 or mBSSP5. The culture of cells and separation and purification of the protein can be carried out by a per se known method.

The present invention also relates to an inhibitor of the novel serine protease of the present invention. Screening of the inhibitor can be carried out according to a per se known method such as comparing the enzyme activity upon bringing into contact with a candidate compound with that without contact with the candidate compound, or the like.

The present invention relates to a non-human transgenic animal whose expression level of hBSSP5 or mBSSP5 gene has been altered. The hBSSP5 or mBSSP5 gene used herein includes cDNA, genomic DNA or synthetic DNA encoding hBSSP5 or mBSSP5. In addition, expression of a gene includes any steps of transcription and translation. The non-human transgenic animal of the present invention is useful for studies of functions or expression control of hBSSP5 or mBSSP5, elucidation of mechanisms of diseases in which hBSSP5 or mBSSP5 is presumed to be involved, and development of disease model animals for screening and safety test of medicine.

In the present invention, expression of a gene can be modified artificially by mutagenizing at a part of several important sites which control normal gene expression (enhancer, promoter, intron, etc.) such as deletion, substitution, addition and/or insertion to increase or decrease an expression level of the gene in comparison with its inherent expression level. This mutagenesis can be carried out according to a known method to obtain the transgenic animal.

In a narrow sense, the transgenic animal means an animal wherein a foreign gene is artificially introduced into reproductive cells by gene recombinant techniques. In a broad sense, the transgenic animal includes an antisense transgenic animal the function of whose specific gene is inhibited by using antisense RNA, an animal whose specific gene is knocked out by using embryonic stem cells (ES cells), and an animal into which point mutation DNA is introduced, and the transgenic animal means an animal into which a foreign gene is stably introduced into a chromosome at an initial stage of ontogeny and the genetic character can be transmitted to the progeny.

The transgenic animal used herein should be understood in a broad sense and includes any vertebrates other than a human being. The transgenic animal of the present invention is useful for studies of functions or expression control of hBSSP5 or mBSSP5, elucidation of mechanisms of diseases associated with cells expressing in a human being, and development of disease model animals for screening and safety test of medicine.

As a technique for creating the transgenic animal, a gene is introduced into a nucleus in a pronucleus stage of egg cells with a micropipette directly under a phase-contrast micro-scope (microinjection, U.S. Pat. No. 4,873,191). Further, there are a method using embryonic stem cell (ES cell), and the like. In addition, there are newly developed methods such as a method wherein a gene is introduced into a retroviral vector or adenoviral vector to infect egg cells, a sperm vector method wherein a gene is introduced into egg cells through sperms, and the like.

A sperm vector method is a gene recombinant technique wherein a foreign gene is incorporated into sperm cells by adhesion, electroporation, etc., followed by fertilization of egg cells to introduce the foreign gene into the egg cells (M. Lavitranoet et al., Cell, 57, 717, 1989). Alternatively, an in vivo site specific gene recombinant technique such as that using cre/loxP recombinase system of bacteriophage P1, FLP recombinase system of *Saccharomyces cerevisiae*, etc. can be used. Furthermore, introduction of a transgene of the desired protein into a non-human animal using a retroviral vector has been reported.

For example, a method for creating a transgenic animal by microinjection can be carried out as follows.

First, a transgene primarily composed of a promoter responsible for expression control, a gene encoding a specific protein and a poly A signal is required. It is necessary to confirm expression modes and amounts between respective systems because an expression mode and amount of a specific molecule is influenced by a promoter activity, and transgenic animals differ from each other according to a particular system due to the difference in a copy number of an introduced transgene and a introduction site on a chromosome. An intron sequence which is spliced may be previously introduced before the poly A signal because it has been found that an expression amount varies due to a non-translation region and splicing. Purity of a gene to be used for introduction into fertilized egg cells should be as high as possible. This is of importance. Animals to be used include mice for collecting fertilized eggs (5- to 6-week-old), male mice for mating, false pregnancy female mice, seminiferous tubule-ligated mice, and the like.

For obtaining fertilized egg cells efficiently, ovulation may be induced with gonadotropin or the like. Fertilized egg cells are recovered and a gene in an injection pipette is injected into male pronucleus of the egg cells by microinjection. For returning the injected egg cells to a fallopian tube, an animal (false pregnancy female mouse, etc.) is provided and about 10 to 15 eggs/mouse are transplanted. Then, genomic DNA is extracted from the end part of the tail to confirm whether the transgene is introduced into newborn mouse or not. This confirmation can be carried out by detection of the transgene with southern blot technique or PCR technique, or by positive cloning wherein a marker gene, which is activated only when homologous recombination is caused, has been introduced. Further, transcribed products derived from the transgene are detected by northern blot technique or RT-PCR technique to confirm expression of the transgene. Or, western blotting can be carried out with a specific antibody to a protein.

The knockout mouse of the present invention is treated so that the function of mBSSP5 gene is lost. A knockout mouse means a transgenic mouse any of whose gene is destroyed by homologous recombination technique so that its function is deficient. A knockout mouse can be created by carrying out homologous recombination with ES cells and selecting embryonic stem cells wherein either of allele genes are modified or destroyed. For example, embryonic stem cells whose genes are manipulated at blastocyte or morula stage of fertilized eggs are injected to obtain a chimera mouse wherein cells derived from the embryonic stem cells are mixed with those derived from the embryo. The chimera mouse (chimera means a single individual formed by somatic cells based on two or more fertilized eggs) can be mated with a normal mouse to create a heterozygote mouse wherein all of either of the allele genes have been modified or destroyed. Further, a homozygote mouse can be created by mating heterozygote mice.

Homologous recombination means recombination between two genes whose nucleotide sequences are the same or very similar to each other in terms of gene recombination mechanism. PCR can be employed to select homologous recombinant cells. A PCR reaction can be carried out by using a part of a gene to be inserted and a part of a region where the insertion is expected as primers to find out occurrence of homologous recombination in cells which give an amplification product. Further, for causing homologous recombination in a gene expressed in embryonic stem cells, homologous recombinant cells can readily be selected by using a known method or its modification. For example, cells can be selected by joining a neomycin resistant gene to a gene to be introduced to impart neomycin resistance to cells after introduction.

The present invention also provide an antibody recognizing hBSSP5 or mBSSP5 or a fragment thereof. The antibody of the present invention includes an antibody against a protein having the amino acid sequence described in SEQ ID NO: 2 or 4 or its fragment. An antibody against hBSSP5 or mBSSP5 or a fragment thereof (e.g., polyclonal antibody, monoclonal antibody, peptide antibody) or an antiserum can be produced by using hBSSP5 or mBSSP5 or a fragment thereof, etc. as an antigen according to a per se known process for producing an antibody or an antiserum.

The hBSSP5 or mBSSP5 or a fragment thereof is administered to a site of a warm-blooded animal where an antibody can be produced by administration thereof as such or together with a diluent or carrier. For enhancing the antibody production, upon administration, Freund's complete adjuvant or Freund's incomplete adjuvant may be administrated. Normally, the administration is carried out once every 1 to 6 weeks, 2 to 10 times in all. Examples of the warm-blooded to be used include monkey, rabbit, dog, guinea pig, mouse, rat, sheep, goat, chicken and the like with mouse and rat being preferred. As rats, for example, Wistar and SD rats are preferred. As mice, for example, BALB/c, C57BL/6 and ICR mice are preferred.

For producing monoclonal antibody producer cells, individuals whose antibody titer have been recognized are selected from warm-blooded animals, e.g., a mouse immunized with an antigen. Two to 5 days after the last immunization, the spleen or lymph node of the immunized animal is collected and antibody producer cells contained therein are subjected to cell fusion with myeloma cells to prepare a monoclonal antibody producer hybridoma. The antibody titer in an antiserum can be determined by, for example, reacting the antiserum with a labeled hBSSP5 or mBSSP5 as described hereinafter, followed by measurement of the activity bound to the antibody. The cell fusion can be carried out according to a known method, for example, that described by Koehler and Milstein (Nature, 256, 495, 1975) or its modifications (J. Immunol. Method, 39, 285, 1980; Eur. J. biochem, 118, 437, 1981; Nature, 285, 446, 1980). As a fusion promoting agent, there are polyethylene glycol (PEG), Sendai virus and the like. Preferably, PEG is used. Further, for improving fusion efficiency, lectin, poly-L-lysine or DMSO can be appropriately added.

Examples of myeloma cells include X-63Ag8, NS-1, P3U1, SP2/0, AP-1 and the like with SP2/0 being preferred.

The preferred ratio of the number of the antibody producer cells (spleen cells):the number of myeloma cells are 1:20 to 20:1. PEG (preferably PEG 1000 to PEG 6000) is added at a concentration of about 10 to 80% and the mixture is incubated at 20 to 40° C., preferably 30 to 37° C. for 1 to 10 minutes to carry out the cell fusion efficiently. Screening of anti-hBSSP5 or mBSSP5 antibody producer hybridomas can be carried out by various methods. For example, a supernatant of a hybridoma culture is added to a solid phase to which hBSSP5 or mBSSP5 antigen is adsorbed directly or together with a carrier (e.g., microplate), followed by addition of an anti-immunoglobulin antibody (in case that the cells used in cell fusion is those of a mouse, anti-mouse immunoglobulin antibody is used) or protein A to detect the anti-hBSSP5 or mBSSP5 monoclonal antibody attached to the solid phase. Or, a supernatant of a hybridoma culture is added to a solid phase to which an anti-immunoglobulin antibody or protein A is adsorbed, followed by addition of hBSSP5 or mBSSP5 labeled with a radioactive substance, an enzyme, etc., to detect the anti-hBSSP5 or mBSSP5 monoclonal antibody attached to the solid phase.

Selection and cloning of the anti-hBSSP or mBSSP monoclonal antibody can be carried out according to a per se known method or its modification. Normally, a HAT (hypoxanthine, aminopterin, thymidine)-added medium for culturing animal cells is used. Any culture medium can be used for selection, cloning and growing up in so far as the hybridoma can grow. For example, there can be used RPMI culture medium containing 1 to 20%, preferably 10 to 20% fetal bovine serum, or a serum-free medium for culturing hybridomas. Preferably, the culture is carried out at a temperature of about 37° C. Normally, the culture time is 5 days to 3 weeks, preferably 1 weeks to 2 weeks. Normally, the culture is carried out under 5% $CO_2$. The antibody titer of a supernatant of a hybridoma culture can be measured according to the same manner as that of the above-described measurement of anti-BSSP5 antibody titer in an antiserum. That is, examples of the measurement to be used include radioimmunoassay (RIA), enzyme-linked immunosorbent assay (ELISA), FIA (fluorescence immunoassay), plaque assay, agglutination reaction method, and the like. Among them, ELISA as shown blew is preferred.

Screening by ELISA

A protein prepared according to the same operation as that for an immunogen is immobilized on the surface of each well of an ELISA plate. Next, BSA, MSA, OVA, KLH, gelatin, skimmed milk, or the like is immobilized on each well to prevent non-specific adsorption. A supernatant of a hybridoma culture is added to each well and is allowed to stand for a given time so that an immunological reaction proceeds. Each well is washed with a washing solution such as PBS or the like. Preferably, a surfactant is added to this washing solution. An enzyme labeled secondary antibody is added and allowed to stand for a given time. As the enzyme to be used for the label, there can be used β-galactosidase, alkaline phosphatase, peroxidase and the like. After washing each well with the same washing solution, a substrate solution of the labeled enzyme used is added so that an enzymatic reaction proceeds. When the desired antibody is present in the supernatant of a hybridoma culture, the enzymatic reaction proceeds and the color of the substrate solution is changed.

Normally, cloning is carried out by a per se known method such as semi-solid agar method, limiting dilution method and the like. Specifically, after confirming a well in which the desired antibody is produced by the above-described method, cloning is carried out to obtain a single clone. For cloning, it is preferred to employ limiting dilution method wherein hybridoma cells are diluted so that one colony is formed per one well of a culture plate. For cloning by limiting dilution method, feeder cells can be used, or a cell growth factor such as interleukin 6, etc. can be added to improve colony forming capability. In addition, cloning can be carried out by using FACS and single cell manipulation method. The cloned hybridoma is preferably cultured in a serum-free culture medium and an optimal amount of an antibody is added to its supernatant. The single hybridoma thus obtained can be cultured in a large amount by using a flask or a cell culture device, or cultured in the abdominal cavity of an animal (J. Immunol. Meth., 53, 313, 1982) to obtain a monoclonal antibody. When culturing in a flask, there can be used a cell culture medium (e.g., IMDM, DMEM, RPMI1640, etc.) containing 0 to 20% of FCS. When culturing in the abdominal cavity of an animal, the animal to be used is preferably the same species or the same line as that from which the myeloma cells used in the cell fusion are derived, a thymus deficient nude mouse or the like, and the hybridoma is transplanted after administration of a mineral oil such as pristane, etc. After 1 to 2 weeks, myeloma cells are proliferated in the abdominal cavity to obtain ascites containing a monoclonal antibody.

The monoclonal antibody of the present invention which does not cross-react with other proteins can be obtained by selecting a monoclonal antibody which recognizes an epitope specific to hBSSP5 or mBSSP5. In general, an epitope presented by an amino acid sequence composed of at least 3, preferably 7 to 20 successive amino acid residues in an amino acid sequence which constitutes a particular protein is said to be an inherent epitope of the protein. Then, a monoclonal antibody recognizing an epitope constituted by a peptide having an amino acid sequence composed of at least 3 successive amino acid residue selected from the amino acid residues disclosed in either of SEQ ID NOS: 2 and 4 can be said to be the monoclonal antibody specific for hBSSP5 or mBSSP5 of the present invention. An epitope common to BSSP5 family can be selected by selecting an amino acid sequence conservative among the amino acid sequences described in SEQ ID NOS: 2 and 4. Or, in case of a region containing an amino acid sequence specific for each sequence, a monoclonal antibody which can differentiate respective proteins can be selected.

Separation and purification of the anti-hBSSP5 or mBSSP5 monoclonal antibody, like a conventional polyclonal antibody, can be carried out according to the same manner as those of immunoglobulins. As a known purification method, there can be used a technique, for example, salting out, alcohol precipitation, isoelectric precipitation, electrophoresis, ammonium sulfate precipitation, absorption and desorption with an ion exchange material (e.g., DEAE), ultrafiltration, gel filtration, or specific purification by collecting only an antibody with an antibody-binding solid phase or an active adsorber such as protein A or protein G, etc., and dissociating the binding to obtain the antibody. For preventing formation of aggregates during purification or decrease in the antibody titer, for example, human serum albumin is added at a concentration of 0.05 to 2%. Alternatively, amino acids such as glycine, α-alanine, etc., in particular, basic amino acids such as lysine, arginine, histidine, etc., saccharides such as glucose, mannitol, etc., or salts such as sodium chloride, etc. can be added. In case of IgM antibody, since it is very liable to be aggregated, it may be treated with β-propionilactone and acetic anhydride.

The polyclonal antibody of the present invention can be produced according to a per se known method or its modification. For example, an immunogen (protein antigen) per se or a complex thereof with a carrier protein is prepared and, according to the same manner as that in the above monoclonal antibody production, a warm-blooded animal is immunized. A material containing an antibody against the protein of the present invention or its fragment is collected from the immunized animal and the antibody is separated and purified to obtain the desired antibody. As for a complex of an immunogen and a carrier protein for immunizing a warm-blooded animal, the kind of a carrier protein and the mixing ratio of a carrier and a hapten are not specifically limited in so far as an antibody against the hapten immunized by cross-linking with the carrier is efficiently produced. For example, there can be used about 0.1 to 20, preferably about 1 to 5 parts by weight of bovine serum albumin, bovine cycloglobulin, hemocyanin, etc. coupled with one part by weight of a hapten. For coupling a carrier and a hapten, various condensing agents can be used. Examples thereof include glutaraldehyde, carbodiimide or maleimide active ester, active ester agents having thiol group or dithiopyridyl group, and the like. The condensed product is administered as such or together with a carrier or diluent to a site of a warm-blooded animal where an antibody can be produced. For enhancing the antibody production, upon administration, Freund's complete adjuvant or Freund's incomplete adjuvant may be administrated. Normally, the administration is carried out once every 2 to 6 weeks, 3 to 10 times in all. The polyclonal antibody can be collected from blood, ascites, or the like, preferably blood of the immunized animal. The polyclonal antibody titer in an antiserum can be measured according to the same manner as measurement of the above monoclonal antibody titer in the antiserum. Separation and purification of the polyclonal antibody, like the above monoclonal antibody, can be carried out according to the same manner as those of immunoglobulins.

The monoclonal antibody and polyclonal antibody against hBSSP5 or mBSSP5 or a fragment thereof can be utilized for diagnosis and treatment of diseases associated with cells expressing hBSSP5 or mBSSP5. By using these antibodies, hBSSP5 or mBSSP5 or a fragment thereof can be determined based on their immunological binding to hBSSP5 or mBSSP5 or a fragment thereof of the present invention. Specifically, examples of a method for determining hBSSP5 or mBSSP5 or a fragment thereof by using these antibodies include a sandwich method wherein the antibody attached to an insoluble carrier and the labeled antibody are reacted with hBSSP5 or mBSSP5 or a fragment thereof to form a sandwich complex and the sandwich complex is detected, as well as a competitive method wherein labeled hBSSP5 or mBSSP5, and hBSSP5 or mBSSP5 or a fragment thereof in the specimen are competitively reacted with the antibody and hBSSP5 or mBSSP5 or a fragment thereof in the specimen is determined based on the amount of the labeled antigen reacted with the antibody.

As a sandwich method for determining hBSSP5 or mBSSP5 or a fragment thereof, there can be used two step method, one step method and the like. In two step method, first, the immobilized antibody is reacted with hBSSP5 or mBSSP5 or a fragment thereof and then unreacted materials are completely removed by washing, followed by addition of the labeled antibody to form immobilized antibody-hBSSP5 or mBSSP5-labeled antibody. In one step method, the immobilized antibody, labeled antibody and hBSSP5 or mBSSP5 or a fragment thereof are added at the same time.

Examples of an insoluble carrier used for the determination include synthetic resins such as polystyrene, polyethylene, polypropylene, polyvinyl chloride, polyester, polyacrylate, nylon, polyacetal, fluorine plastic, etc.; polysaccharides such as cellulose, agarose, etc.; glass; metal; and the like. An insoluble carrier may be shaped in various forms, for example, tray, sphere, fiber, rod plate, container, cell, test tube, and the like. The antibody adsorbed by a carrier is stored at a cold place in the presence of an appropriate preservative such as sodium azide or the like.

For immobilization of the antibody, a known chemical bonding method or a physical adsorption can be used. Examples of a chemical bonding method include a method using glutaraldehyde; maleimide method using N-succusinimidyl-4-(N-maleimidomethyl)cyclohexane-1-carboxylate, N-succusinimidyl-2-maleimide acetate or the like; carbodiimide method using 1-ethyl-3-(3-dimethylaminopropyl)carbodiimide hydrochloride; or the like. In addition, there are maleimidobenzoyl-N-hydroxysuccinimide ester method, N-succinimidyl-3-(2-pyridylthio)propionic acid method, bisdiazobenzidine method, and dipalmityllysine method. Or, it is possible to capture a complex formed beforehand by reacting a materiel to be tested with two antibodies, whose epitopes are different, with an immobilized a 3rd antibody against the antibody.

For labeling, it is preferred to use enzyme, fluorescent substance, luminous substance, radioactive substance, metal chelate, or the like. Examples of the enzyme include peroxidase, alkaline phosphatase, β-D-galactosidase, malate dehydrogenase, *Staphylococcus* nuclease, δ-5-steroidisomerase, α-glycerol phosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholinesterase and the like. Examples of the fluorescent substance include fluorescein isothiocyanate, phycobiliprotein, rhodamine, phycoerythrin, phycocyanin, allophycocyanin, o-phthalaldehyde, and the like. Examples of the luminous substance include isoluminol, lucigenin, luminol, aromatic acridinium ester, imidazole, acrdinium salt and its modified ester, luciferin, luciferase, aequorin and the like. Examples of the radioactive substance include $^{125}I$, $^{127}I$, $^{131}I$, $^{14}C$, $^{3}H$, $^{32}P$, $^{35}S$ and the like. The labeling material is not limited to them and any material which can be used for immunological determination can be used. Further, a low molecular weight hapten such as biotin, dinitrophenyl, pyridoxal or fluorescamine may be attached to the antibody. Preferably, horseradish peroxidase is used as a labeling enzyme. This enzyme can be reacted with various substrates and can readily be attached to the antibody by periodate method.

When an enzyme is used as a labeling material, a substrate and, if necessary, a coloring enzyme is used for measuring its activity. In case of using peroxidase as the enzyme, $H_2O_2$ is used as a substrate and, as a coloring agent, there can be used 2,2'-azino-di-[3-ethylbenzthiazoline sulfonic acid] ammonium salt (ABTS), 5'-aminosalicylic acid, o-phenylenediamine, 4-aminoantipyrine, 3,3',5,5'-tetramethylbenzidine and the like. In case of using alkaline phosphatase as the enzyme, o-nitorphenylphosphate, p-nitrophenylphosphoric acid, or the like can be used as a substrate. In case of using β-D-galactosidase as the enzyme, fluorescein-d-(β-D-galactopyranoside), 4-methylumbelliphenyl-β-D-galactopyranoside, or the like can be used as a substrate. The present invention also include a kit comprising the above monoclonal antibody, polyclonal antibody and reagents.

As a cross-linking agent, a known cross-linking agent such as N,N'-o-phenylenedimaleimide, 4-(N-maleimidomethyl)cyclohexanoate N-succinimide ester, 6-maleimidohexanoate N-succineimide ester, 4,4'-dithiopyridine or the like can be utilized. The reaction of these cross-linking agents with enzymes and antibodies can be carried out by a known method according to properties of a particular cross-linking agent. Further, as the antibody, a fragment thereof, for example, Fab', Fab, F(b'2) can be used as the case may be. A labeled enzyme can be obtained by the same treatment regardless of whether the antibody is polyclonal or monoclonal. When the above labeled enzyme obtained by using a cross-linking agent is purified by a known method such as affinity chromatography or the like, a immunoassay system having more higher sensitivity can be obtained. The enzyme labeled and purified antibody is stored at a dark cold place with addition of a stabilizer such as thimerosal, glycerin or after lyophilization.

An objective to be determined is not specifically limited in so far as it is a sample containing hBSSP5 or mBSSP5 or a fragment thereof, or a sample containing a precursor or a fragment thereof and includes body fluids such as plasma, serum, blood, serum, urine, tissue fluid, cerebrospinal fluid and the like.

When a blood level of BSSP5 in a rat pancreatitis model by using the above-obtained antibody against hBSSP5 or mBSSP5 or its fragment, increase in the blood level was observed. This shows that the anti-BSSP5 antibody can be used to detect pancreatitis.

The following Examples further illustrate the present invention in detail but are not construed to limit the scope thereof.

EXAMPLE 1

Cloning of Novel Serine Proteases

The cloning was carried out by PCR using a human brain cDNA library (Clontech) as a template and nucleotide sequences corresponding to an amino acid sequence common to serine proteases represented by Primer 1: GTG CTC ACN GCN GCB CAY TG (SEQ ID NO: 14)
Primer 2: CCV CTR WSD CCN CCN GGC GA (SEQ ID NO: 15)

as primers. Namely, 5 μl of the template, 5 μl of 10×ExTaq buffer, 5 μl of dNTP, 10 pmol of each of the above primers and 0.5 μl of ExTaq (TAKARA) were added and the total volume was adjusted to 50 μl with sterilized water. PCR was carried out by repeating a cycle of heating at 94° C. for 0.5 minute, at 55° C. for 0.5 minute and then at 72° C. for 1 minutes, 35 times. The PCR product was mixed with pCR II-TOPO vector attached to TOPO TA cloning kit (Invitrogen) and the mixture was allowed to stand at room temperature for 5 minutes. Then, according to a conventional manner, E. coli Top 10 attached to the kit was transformed and applied to a LB (Amp$^+$) plate (containing 100 μg/ml of ampicillin). According to a conventional manner, a plasmid was extracted from each colony obtained and its nucleotide sequence was determined by cycle sequencing method with a fluorescence sequencer (ABI). Homology of the sequence of each clone was examined by means of GenBank. Regarding an unknown sequence, i.e., BSSP5 gene, the full length cDNA was obtained by 5' RACE and 3' RACE and, according to the same manner as described above, the nucleotide sequence was determined. Namely, BSSP5 clone specific primers, GSP1 primers (primers having nucleotide sequences of SEQ ID NOS: 16 and 18) and GSP2 primers [primers having SEQ ID NOS: 17 and 19) were prepared. PCR was carried out by using human brain Marathon-Ready cDNA (Clontech), AP1 primer attached to this reagent and the above GSP1 primer and heating at 94° C. for 2 minutes once and repeating a cycle of heating at 94° C. for 30 seconds, at 60° C. for 30 seconds and then at 72° C. for 30 seconds 35 times. Then, 5 μl of the PCR product diluted to 1/100, 5 μl of 10× buffer, 5 μl of dNTP, 10 pmol of either of 10 μM of the above GSP2 primer, 10 pmol of AP2 primer attached to the above reagent and 0.5 unit of ExTaq were admixed and adjusted to 50 μl with sterilized water. Then, according to the same manner as the above, PCR was carried out. The PCR product was cloned by the above TOPO TA cloning kit and sequenced to obtain the upstream and downstream regions of the above clone. Further, based on this sequence, the primers capable of amplifying ORF [hBSSP5F1 (SEQ ID NO: 20), hBSSP5R1/E (SEQ ID NO: 22)] were prepared and PCR carried out using human brain Marathon-ready cDNA as a template to confirm that these clones were identical. This was cloned into pCR II-TOPO vector attached to TOPO TA cloning kit to obtain the plasmid pCR II/hBSSP5 containing the full length cDNA clone. The nucleotide sequence of DNA contained in this plasmid is shown in SEQ ID NO: 1 and the amino acid sequence of hBSSP5 protein deduced from the nucleotide sequence is shown in SEQ ID NO: 2.

According to the same manner, the plasmid pCRII/mBSSP5 containing a mouse homologous gene was obtained by carrying out 5' RACE and 3' RACE using mouse brain Marathon-Ready cDNA (Clontech) as a template, followed by cloning. The nucleotide sequence contained in this plasmid is shown in SEQ ID NO: 3 and the amino acid sequence deduced from this nucleotide sequence is shown in SEQ ID NO: 4. The amino acid sequence shown in SEQ ID NO: 4 is mBSSP5 protein composed of 264 amino acids and the nucleotied sequence encoding this protein shown in SEQ ID NO 3 is composed of 792 bases. The sequence represented by the −33rd to −1st amino acids of SEQ ID4: is a prepro or pro part and the amino acid sequence represented by the −33rd to 231st amino acids is considered to be a precursor of mBSSP5 protein.

| SEQ ID NO: | Name of primer | Direction | Sequence | Use |
|---|---|---|---|---|
| human BSSP5 | | | | |
| 16 | | Forward | TGTCAGCCCTGGCCGCCATT | RACE |
| 17 | | Forward | GCGAGTATGACCGATCATCA | RACE |
| 18 | | Reverse | CGCCACCTGCACAGATCATG | RACE |
| 19 | | Reverse | GAATCAGTGCCGGCAGTACT | PACE |
| 20 | hBSSP5F1 | Forward | TGCCACGATGTTGCTGCTCA | FL* |

-continued

| SEQ ID NO: | Name of primer | Direction | Sequence | Use |
|---|---|---|---|---|
| 21 | hBSSP5F2 | Forward | ATTGTCAACGGGGAGAATGC | mature |
| 22 | hBSSP5R1/E | Reverse | GGAATTCGGGTCTTTAATGGGTTGAGC | FL* |
| 23 | hBSSP5R4 | Reverse | CCTGGCACGAGGAGGCAC | for RT-PCR |
| mousse BSSP5 | | | | |
| 24 | mBSSP5F1 | Forward | ACCATGAACAATGACCTGAC | RACE |
| 25 | mBSSP5F2 | Forward | GAATCAGTGTCGGCAGT | RACE |
| 26 | mBSSP5F3 | Forward | GACCATCTCAACACCATTCC | FL* |
| 27 | mBSSP5Fmature | Forward | ATTGTCAACGGGGAGAATGC | mature |
| 28 | mBSSP5.1 | Reverse | ATGGCATCGGTAATGCGTGC | RACE |
| 29 | mBSSP5R2 | Reverse | CAGGTGTTTCCCTTCTGGCA | RACE |
| 30 | mBSSP5R3/E | Reverse | GGAATTCGGACAGTTTAGTTGTAGGCC | FL* |

*for full length

EXAMPLE 2

Expression of hBSSP5 or mBSSP5 Gene in Human Beings or Mice Internal Organs

According to the protocol of QuickPrep Micro mRNA purification Kit (Amersham-Pharmacia), mRNAs were isolated from various internal organs of Balb/c mice or their fetuses. They were subjected to electrophoresis according to a conventional manner and transcribed to a nylon membrane. A probe was prepared separately by isolating a part of a nucleotide sequence encoding the mature protein of mBSSP5 (the 132nd to 824th bases of SEQ ID NO: 3) from pCR II/mBSSP5, purifying it and labeling it with $\alpha$-$^{32}$P dCTP. The probe was diluted with 5×SSC and reacted with the above membrane filter at 65° C. for a whole day and night. According to the same manner, a probe was prepared by isolating a part of a nucleotide sequence encoding the mature protein of hBSSP5 (the 110th to 802nd bases of SEQ ID NO: 1) from pCR II/hBSSP5, purifying it and labeling it with $\alpha$-$^{32}$P dCTP. The probe was diluted with 5×SSC and reacted with human multiple tissue blot (Clontech) membrane at 65° C. for a whole day and night. Then, each membrane filter was washed twice each with 2×SSC/0.1% SDS at room temperature for 30 minutes, 1×SSC/0.1% SDS at room temperature for 30 minutes and 0.1×SSC/0.1% SDS at 65° C. for 30 minutes. The filter was exposed to an imaging plate for FLA2000 (Fuji Film) for one day to analyze the expression. The results shown in the drawings are those obtained by using human multiple tissue blot (clontech) membrane (FIG. 1) and mRNAs prepared from various internal organs of 3-month-old mice (FIG. 2). In addition, the mRNAs prepared above were subjected to RT-PCR by using Ready To Go RT-PCR Beads (Amersham-Pharmacia) and hBSSP5 or mBSSP5 gene specific primers according to the protocol attached to the kit (amplification by using SEQ ID NOS: 20 and 22 and further amplification by using SEQ ID NOS: 21 and 23).

Figure 2:
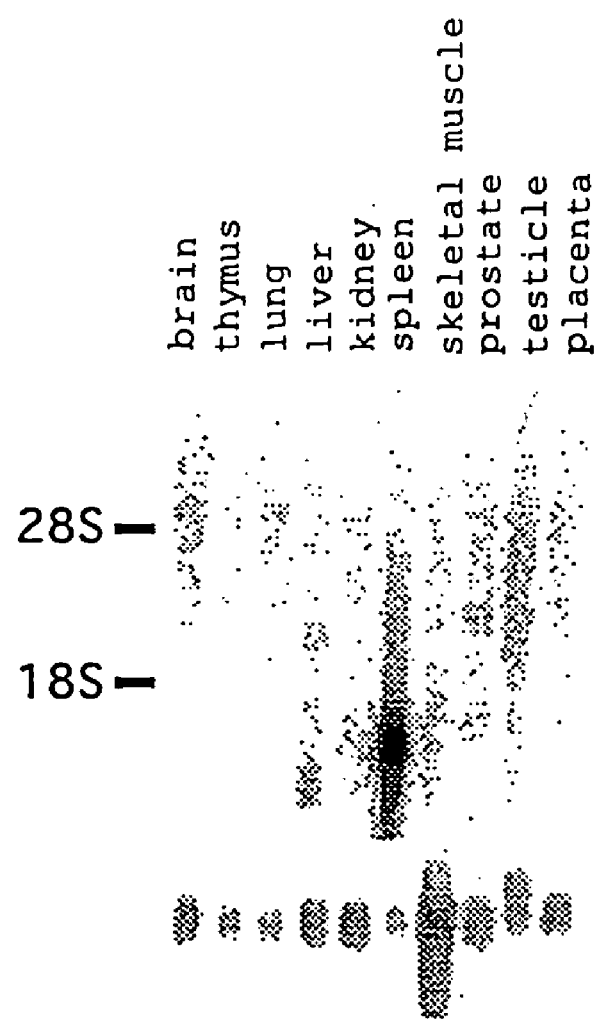
FIG. 2 illustrates the results of northern blotting using mRNAs prepared from various internal organs of mice.

As seen from FIGS. 1 and 2, in case of northern blotting analysis, the expression of hBSSP5 was observed in pancreas and the expression of mBSSP5 was observed in spleen. Further, in case of RT-PCR, the expression of hBSSP5 was observed in brain of fetuses and in placenta in adults. The expression of mBSSP5 was observed in brain and testicle of fetuses to grown up mice. Then, it is presumed that the novel serine proteases have various roles in brain, placenta, pancreas, spleen and tenticle.

EXAMPLE 3

Determination of Enzyme Activity of Novel Serine Protease Mature Protein Encoded by hBSSP5 or mBSSP5 Gene (1) Construction of Expression Plasmid A cDNA fragment containing the region encoding the mature protein of hBSSP5 or mBSSP5 protein was amplified by PCR using the plasmid pCR II/hBSSP5 or pCR II/mBSSP5 as a template (the primers used were SEQ ID NOS: 21 and 22 for human being, and SEQ ID NOS: 27 and 30 for mouse). Each PCR product was ligated to pTrc-HisB (Invitrogen) which had been digested with BamHI and blunted with mung bean nuclease according to a conventional method. E. coli JM109 was transformed by the resultant and colonies formed were analyzed by PCR to obtain E. coli containing the desired serine protease expressing plasmid pTricHis/hBSSP5 or pTrcHis/mBSSP5.

The resultant E. coli strains were designated E. coli pTrcHis/hBSSP5 and E. coli pTrcHis/mBSSP5 and deposited at National Institute of Bioscience and Human-Technology (NIBH), Agency of Industrial Science & Technology of 1-1-3 Higashi, Tsukuba-shi, Ibaraki-ken, Japan on Oct. 29, 1998 under the accession numbers of FERM P-17038 and FERM P-17035, respectively.

(2) Expression of Protein by E. coli Containing Expression Plasmid

A single colony of E. coli having the expression plasmid was inoculated in 10 ml of LB (Amp$^+$) culture medium and incubated at 37° C. overnight. This was inoculated in 250 ml of LB (Amp$^+$) culture medium and incubated at 37° C. When the absorbance at 600 nm became 0.5, 250 $\mu$l of 0.1 M IPTG (isopropyl-$\beta$-D-(−)-thiogalactopyranoside) was added and the incubation was continued for additional 5 hours. The E. coli was centrifuged and suspended in a cell disruption buffer (10 mM phosphate buffer pH 7.5, 1 mM EDTA) and sonicated on ice to disrupt E. coli. This was centrifuged at 14,000 r.p.m. at 4° C. for 20 minutes to obtain a precipitate. The precipitate was washed twice with a cell disruption buffer containing 0.5% Triton X-100™ and washed with water to remove Triton X-100™. Then, the resultant mixture was dissolved by soaking in a denaturation buffer containing 8 M urea (8M urea, 50 mM Tris pH8.5, 20 mM 2ME) at 37° C. for 1 hour. The solution was passed through TALON metal affinity resin (Clontech), washed with the denaturation buffer containing 10 mM imidazole, and then eluted with the denaturation buffer containing 100 mM imidazole to purify the solution. The purified product was dialyzed against PBS for 3 days with exchanging the buffer every other night to obtain the protein hBSSP5-His or mBSSP5-His.

EXAMPLE 4

Expression of Novel Serine Protease Mature Protein Encoded by BSSP5 Gene by Using pFBTrypSigTag/hBSSP5

(1) Construction of pFBTrypSigTag/hBSSP5

The sequences represented by SEQ ID NOS: 5 and 6 were subjected to annealing and digested with NheI and BamHI. The resultant fragment was inserted into NheI-BamHI digested pSecTag2A (Invitrogen) to obtain pSecTrypHis. Twenty units of BamHI was added to 5 µg of pSecTrypHis vector and the vector was cleaved at 37° C. over 4 hours. Then, 6 units of mung bean nuclease (TAKARA) was added thereto and reacted at room temperature (25° C.) for 30 minutes to blunt the terminal ends. Further, the 3'-terminus side of the cloning site was cleaved with 20 units of XhoI, 1 unit of bacterial alkaline phosphatase (TAKARA) was added thereto and the reaction was carried out at 65° C. for 30 minutes.

Figure 3:
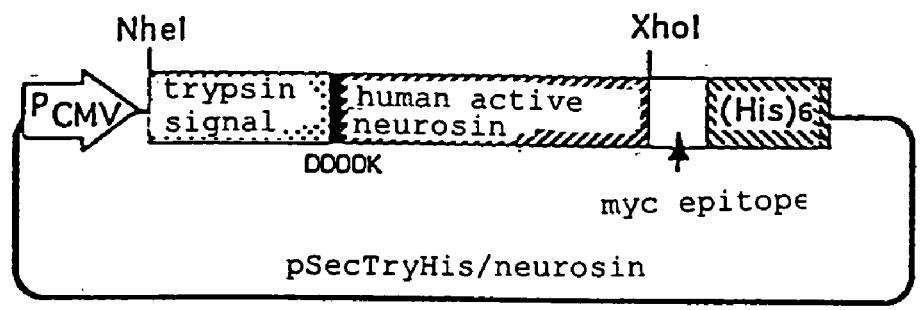
FIG. 3 is a plasmid constructed by the method of Example 4 hereinafter.

According to the same manner as that described in JP 9-149790 A or Biochim. Biophys. Acta, 1350, 11, 1997, mRNA was prepared from COLO201 cells and cDNA was synthesized to obtain the plasmid pSPORT/neurosin. cDNA of an active region of neurosin was obtained from pSPORT/neurosin by PCR using primers having the sequences represented by SEQ ID NOS: 7 and 8. Ten units of XhoI was reacted with the PCR product at 37° C. for 3 hours to cleave XhoI site at the 3'-side thereof. This was inserted into pSecTrypHis by TAKARA ligation kit to obtain pSecTrypHis/neursoin (FIG. 3).

Amplification was carried out by using the primers having the sequences represented by SEQ ID NOS: 9 and 10 so that the peptide of Leu-Val-His-Gly was present at the C-terminus of the part from trypsin signal to the enterokinase recognition site of pSecTrypHis/neurosin. This was inserted between NheI and HindIII sites of pSecTag2A to construct the plasmid pTrypSig.

One µg (0.1 µl) of the plasmid pSecTab2A was treated with the restriction enzymes NheI and BamHI to completely remove a region encoding the leader sequence of IgGk. One hundred pmol portions of DANs represented by SEQ ID NOS: 31 and 32 were added to the resultant solution and the mixture was heated at 70° C. for 10 minutes and subjected to annealing by allowing to stand at room temperature for 30 minutes. Two µl of I solution of DNA ligation kit Ver. 2 (TAKARA) was added to 1 µl portions of His secretory signal sequence and pSecTag2A treated by NheI and BamHI and the reaction was carried out at 16° C. for 30 minutes.

To the reaction mixture was add 0.1 ml of E. coli competent cell XL1-Blue (STRATAGENE) and reacted on ice for 30 minutes. Then, the reaction mixture was subjected to heat shock at 42° C. for 60 seconds. After standing on ice for 2 minutes, 0.9 ml of SOC culture medium (Toyo Boseki K. K.) was added thereto and the mixture was shaken with a shaker at 37° C. for 1 hour. The mixture was centrifuged at 5,000 r.p.m. for 1 minutes and the supernatant was discarded. The precipitated competent cells were suspended in the liquid remained in the centrifuge tube and the suspension was applied to 2 ampicillin LB plates containing 100 µg/ml of ampicillin in the ratio of 1:10. The plates were incubated at 37° C. overnight. Among the colonies formed, a colony into which DNA of His secretory signal was inserted was selected by PCR to obtain pTrypHis.

Figure 4:
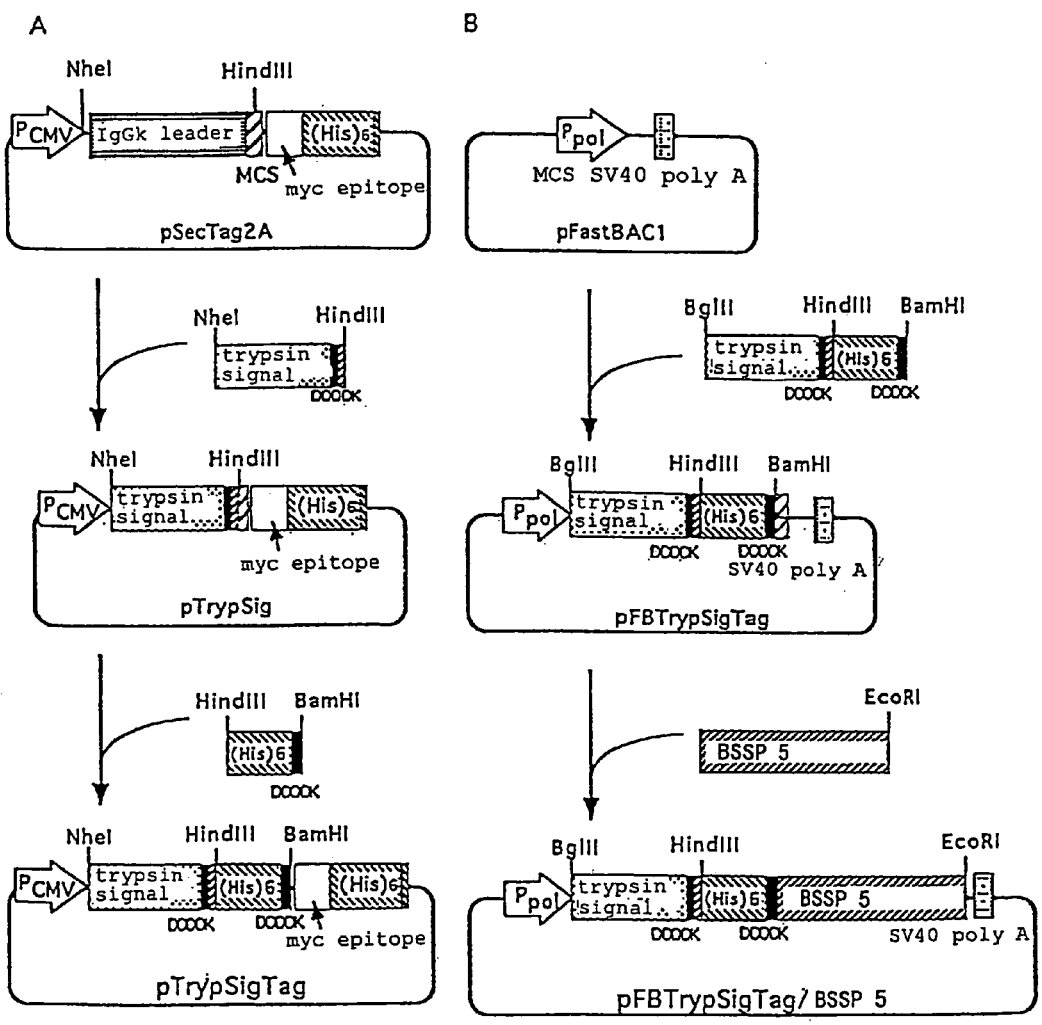
FIG. 4 illustrates the construction of plasmid according to the method of Example 4 hereinafter.

A sequence of about 200 bp containing His Tag region of pTrypHis was amplified by using primers having the sequence represented by SEQ ID NOS: 10 and 11 and a fragment of about 40 bp containing His Tag and enterokinase recognizing site formed by digestion of HindIII and BamHI was inserted into pTrypSig to construct pTrypSigTag (FIG. 4A).

cDNA was prepared by PCR of the sequence from trypsin signal to enterokinase recognizing site of pTrypSigTag using primers having the sequences represented by SEQ ID NOS 8 and 12 and cut out by digestion with BglII and BamHI. It was inserted into BamHI site of pFastBAC1 (GIBCO). The insertion direction was confirmed by PCR using primers having the sequences represented by SEQ ID NOS 8 and 13. A clone into which the cDNA was inserted in the direction toward transcription and translation by polyhedrin promoter was selected to obtain pFBTrypSigTag.

Twenty units of BamHI was added to 5 µg of pFBTrypSigTag vector and the vector was cleaved at 37° C. over 4 hours, followed by addition of 6 units of mung bean nuclease (TAKARA) and reaction at room temperature (25° C.) for 30 minutes to blunt the terminal ends. Further, the 3'-side of the cloning site was cleaved by 20 units of EcoRI, followed by addition of 1 unit of bacterial alkaline phosphatase (TAKARA). The reaction was carried out at 65° C. for 30 minutes.

cDNA of the active region of hBSSP5 was obtained from pTrcHis/hBSSP5 prepared from E. coli pTrcHis/hBSSP5 (accession No. FERM P-17038) or pCRII/hBSSP5 by PCR according to a conventional manner. The resultant cDNA was inserted into pFBTrypSigTag to obtain pFBTrypSigTag/hBSSP5 (FIG. 4B). At this time, correct insertion of hBSSP5 was confirmed by determining the sequence.

Bacmid DNA was transformed with PFBTrypSigTag/hBSSP5 according to a protocol of Gibco BRL BAC-TO-BAC baculovirus expression system to prepare a recombinant bacmid having chimera hBSSP5 fused with trypsinogen signal peptide, His tag and enterokinase recognizing site. When this was expressed in Sf-9 cell according to a manual of BAC-TO-BAC baculovirus expression system, it was secreted in the culture supernatant from 2 days after infection of the virus.

According to the same manner as described above, pFBTrypSigTag/mBSSP5 can be prepared and secreted by using pTrcHis/mBSSP5 obtained from E. coli pTricHis/mBSSP5 (accession No. FERM P-17035) or pCRII/mBSSP5 obtained in Example 1.

(2) Determination of Enzyme Activity

The recombinant fused protein hBSSP5 obtained in the culture supernatant was passed through a chelate column to purify it and, after dialysis, its enzyme activity was determined. First, the culture supernatant was applied to a chelate column (Ni-NTA-Agarose, Qiagen) with PBS buffer and eluted stepwise with a solution of imidazole (Wako Pure Chemical Industries, Ltd.) dissolved in PBS. The resultant imidazole-eluted fraction was applied to a PD-10 column (Pharmacia) to exchange to PBS buffer. Fifty µl of this sample was mixed with 10 µl of enterokinase (1 U/1 µl, Invitrogen) and the reaction was carried out at room temperature for 60 minutes. Each of various synthetic substrates (Peptide Laboratory, Boc-Gln-Ala-Arg-MCA, Boc-Phe-Ser-Arg-MCA, Bz-Arg-MCA, Boc-Val-Leu-Lys-MCA, Pyr-Gly-Arg-MCA, Pro-Phe-Arg-MCA, Boc-Val-Pro-Arg-MCA, Z-Arg-Arg-MCA, Arg-MCA, Z-Phe-Arg-MCA) was dissolved in DMSO and diluted with 1 M Tris-HCl (pH 8.0) to obtain a substrate solution. Fifty µl of 0.2 M substrate solution was added thereto and further the reaction was carried out at 37° C. After one hour, the fluorescence of AMC (7-amino-4-methylcoumalin) formed by the enzymatic reaction was measured at 380 nm of excitation wavelength and 460 nm of fluorescence wavelength to determine the activity.

As a result, the recombinant fused protein hBSSP5 has been shown to have serine protease activity. Likewise, mBSSP5 derived from a mouse showed the activity.

EXAMPLE 5

Detection of BSSP5 in Urine

Figure 5:
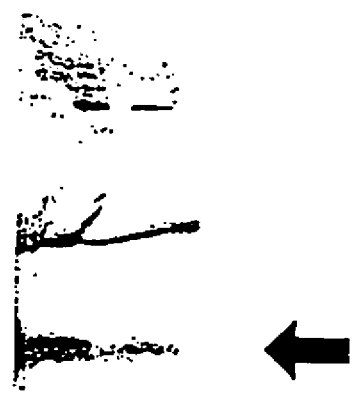
FIG. 5 illustrates the presence of BSSP5 in urine.
Figure 6:
FIG. 6 illustrates the variation in blood BSSP5 level in a rat pancreatitis model.

Urine samples were collected from human beings and rats. According to a conventional method, 10 μl of each sample was subjected to electrophoresis on 12.5% SDS-polyacrylamide gel and then blotted on PVDF membrane (1 mmobilon P, Millipore). After blocking the filter with skimmed milk, and reacted with an anti-BSSP5 antibody diluted 1,000-fold or 10,000-fold with Tween-PBS at room temperature for several hours to overnight. The filter was washed with Tween-PBS three times and reacted with alkaline phosphatasse labeled anti-rabbit IgG, followed by washing Tween-PBS in the same manner. When the filter was colored by dipping in BCIP/NBT solution, BSSP5 bands having the presumed molecular weight were detected in the human bening and rat samples (FIG. 5).

The anti-BSSP5 antibody was a peptide antibody against hBSSP5. The antibody was prepared as follows.

Namely, peptides were synthesized by adding one cysteine to C-terminus sides of the peptides composed of the 56th to 73rd amino acids (Glu Tyr Asp Arg Ser Ser Asn Ala Glu Pro Leu Gln Val Leu Ser Val Ser Arg) and the 207th to 225th amino acids (Asn Val Arg Ala Pro Ala Val Tyr Thr Arg Val Ser Lys Phe Ser Thr Trp Ile Asn) of SEQ ID NO: 2. Separately, hemocyanin (KLH) was reacted with a cross-linking agent, m-maleimidobenzoyl-N-hydrosuccinimide ester (MBS) to prepare a KLH-MB complex. The KLH-MB was reacted each synthetic peptide to obtain two immunogens. The resultant immunogen was administered to a rabbit together with Freund's complete adjuvant once. Then, booster immunization was conducted together with Freund's incomplete adjuvant every two weeks three times in all. Four days after the last booster immunization, a blood sample was collected. The serum obtained was purified by protein A column to obtain a peptide antibody against hBSSP5.

Reactivity of each peptide antibody to BSSP5 was confirmed. The anti-BSSP5 antibody used in Example 5 and the following Example 6 is a mixture of these two peptide antibodies.

EXAMPLE 6

Variation in Blood BSSP5 in Rat Pancreatitis Model

According to a conventional manner, pancreatitis was induced in 4 to 6-week-old rats with cerulein. Blood samples were collected before inducing pancreatitis and 6, 12 and 24 hours after incuding pancreatitis to recover serum samples. Serum albumin was removed by mixing with Blue Sepharose (Amersham Pharmacea) and, according to the same manner as in Example 1, 10 μl of the serum was subjected to SDS-PAGE western blotting, followed by detection with the anti-BSSP 5 antibody. As a result, although BSSP5 was present even in a healthy state, 12 hours after inducing pancreatitis, temporary increase in blood BSSP5 was observed and this showed the possibility of detection of pancreatitis by measureing blood BSSP5.

INDUSTRIAL UTILITY

According to the present invention, there are provided isolated human and mouse serine protease (hBSSP5 and mBSSP5) polynucleotides, their homologous forms, mature forms, precursors and polymorphic variants. Further, according to the present invention, there are provided hBSSP5 and mBSSP5 proteins as well as compositions containing hBSSP5 and mBSSP5 polynucleotides and proteins, their production and use.

Sequence Listing Free Text

SEQ ID NO: 5: Designed oligonucleotide to construct plasmid pSecTrypHis

SEQ ID NO: 6: Designed oligonucleotide to construct plasmid pSecTrypHis

SEQ ID NO: 7: Designed oligonucleotide primer to amplify neurosin-encoding sequence SEQ ID NO: 8: Designed oligonucleotide primer to amplify neurosin-encoding sequence SEQ ID NO: 9: Designed oligonucleotide primer to amplify a portion of plasmid pSecTrypHis/Neurosin SEQ ID NO: 10: Designed oligonucleotide primer to amplify a portion of plasmid pSecTrypHis/Neurosin SEQ ID NO: 11: Designed oligonucleotide primer to amplify a portion of plasmid pTrypHis SEQ ID NO: 12: Designed oligonucleotide primer to amplify a portion of plasmid pTrypSigTag SEQ ID NO: 13: Designed oligonucleotide primer to amplify a portion of plasmid pFBTrypSigTag SEQ ID NO: 14: Designed oligonucleotide primer to amplify conserved region of serin proteases-encoding sequence; n is a, c, g or t.

SEQ ID NO: 15: Designed oligonucleotide primer to amplify conserved region of serin proteases-encoding sequence; n is a, c, g or t.

SEQ ID NO: 16: Designed oligonucleotide primer for RACE for hBSSP5 (forward)

SEQ ID NO: 17: Designed oligonucleotide primer for RACE for hBSSP5 (forward)

SEQ ID NO: 18: Designed oligonucleotide primer for RACE for hBSSP5 (reverse)

SEQ ID NO: 19: Designed oligonucleotide primer for RACE for hBSSP5 (reverse)

SEQ ID NO: 20: Designed oligonucleotide primer designated as hBSSP5F1 to amplify full length hBSSP5 (forward)

SEQ ID NO: 21: Designed oligonucleotide primer designated as hBSSP5F2 to amplify mature hBSSP5-encoding region (forward)

SEQ ID NO: 22: Designed oligonucleotide primer designated as hBSSP5R1/E to amplify full length hBSSP5 (reverse)

SEQ ID NO: 23: Designed oligonucleotide primer designated as hBSSP5R4 for RT-PCR (reverse)

SEQ ID NO: 24: Designed oligonucleotide primer designated as mBSSP5F1 for RACE for mBSSP5 (forward)

SEQ ID NO: 25: Designed oligonucleotide primer designated as mBSSP5F2 for RACE for mBSSP5 (Forward)

SEQ ID NO: 26: Designed oligonucleotide primer designated as mBSSP5F3 to amplify full length mBSSP5 (forward)

SEQ ID NO: 27: Designed oligonucleotide primer designated as mBSSP5Fmature to amplify mature mBSSP5-encoding region (forward)
SEQ ID NO: 28: Designed oligonucleotide primer designated as mBSSP5.1 for RACE for MBSSP5 (reverse)
SEQ ID NO: 29: Designed oligonucleotide primer designated as mBSSP5R2 for RACE for mBSSP5 (reverse)
SEQ ID NO: 30: Designed oligonucleotide primer designated as mBSSP5R3/E to amplify full length mBSSP5 (reverse)
SEQ ID NO: 31: Designed oligonucleotide to construct plasmid pTrypHis
SEQ ID NO: 32: Designed oligonucleotide to construct plasmid pTrypHis

What is claimed is:

1. A method for detecting pancreatitis, comprising:
measuring the concentration, in the blood or urine of an individual, of a protein selected from the group consisting of:

(i) a protein comprising the amino acid sequence of residues 1–231 of SEQ ID NO:2, and having serine protease activity; and (ii) a protein comprising the amino acid sequence of residues 1–231 of SEQ ID NO:4, and having serine protease activity, by contacting the blood or the urine with an antibody, raised against an antigen consisting of amino acid residues 1–231 of either SEQ ID NO:2 or SEQ ID NO:4, or an antigenic fragment thereof, to immunologically bind any of said protein or fragment thereof in the blood or the urine; and detecting pancreatitis by determining if the concentration of the protein or fragment thereof represents an increased level of the protein or fragment thereof in the blood or urine of the individual when the concentration of the protein or fragment thereof is compared before and after induction of pancreatitis in the individual.

* * * * *

SEQUENCE LISTING

```
<160> NUMBER OF SEQ ID NOS: 32

<210> SEQ ID NO 1
<211> LENGTH: 1149
<212> TYPE: DNA
<213> ORGANISM: Homo sapiens
<220> FEATURE:
<221> NAME/KEY: CDS
<222> LOCATION: (11)..(802)
<223> OTHER INFORMATION:
<220> FEATURE:
<221> NAME/KEY: mat_peptide
<222> LOCATION: (110)..()
<223> OTHER INFORMATION:

<400> SEQUENCE: 1
atctgccacg atg ttg ctg ctc agc ctg acc cta agc ctg gtt ctc ctc         49
            Met Leu Leu Leu Ser Leu Thr Leu Ser Leu Val Leu Leu
                -30                 -25 ggc tcc tcc tgg ggc tgc ggc att cct gcc atc aaa ccg gca ctg agc        97
Gly Ser Ser Trp Gly Cys Gly Ile Pro Ala Ile Lys Pro Ala Leu Ser
-20             -15                 -10                 -5 ttc agc cag agg att gtc aac ggg gag aat gca gtg ttg ggc tcc tgg       145
Phe Ser Gln Arg Ile Val Asn Gly Glu Asn Ala Val Leu Gly Ser Trp
        -1  1                    5                      10 ccc tgg cag gtg tcc ctg cag gac agc agc ggc ttc cac ttc tgc ggt       193
Pro Trp Gln Val Ser Leu Gln Asp Ser Ser Gly Phe His Phe Cys Gly
            15                  20                  25 ggt tct ctc atc agc cag tcc tgg gtg gtc act gct gcc cac tgc aat       241
Gly Ser Leu Ile Ser Gln Ser Trp Val Val Thr Ala Ala His Cys Asn
        30                  35                  40 gtc agc cct ggc cgc cat ttt gtt gtc ctg ggc gag tat gac cga tca       289
Val Ser Pro Gly Arg His Phe Val Val Leu Gly Glu Tyr Asp Arg Ser
45                  50                  55                  60 tca aac gca gag ccc ttg cag gtt ctg tcc gtc tct cgg gcc att aca       337
Ser Asn Ala Glu Pro Leu Gln Val Leu Ser Val Ser Arg Ala Ile Thr
                65                  70                  75 cac cct agc tgg aac tct acc acc atg aac aat gac gtg acg ctg ctg       385
His Pro Ser Trp Asn Ser Thr Thr Met Asn Asn Asp Val Thr Leu Leu
            80                  85                  90 aag ctc gcc tcg cca gcc cag tac aca aca cgc atc tcg cca gtt tgc       433
Lys Leu Ala Ser Pro Ala Gln Tyr Thr Thr Arg Ile Ser Pro Val Cys
        95                  100                 105 ctg gca tcc tca aac gag gct ctg act gaa ggc ctc acg tgt gtc acc       481
Leu Ala Ser Ser Asn Glu Ala Leu Thr Glu Gly Leu Thr Cys Val Thr
    110                 115                 120 acc ggc tgg ggt cgc ctc agt ggc gtg ggc aat gtg aca cca gca cat       529
Thr Gly Trp Gly Arg Leu Ser Gly Val Gly Asn Val Thr Pro Ala His
125                 130                 135                 140 ctg cag cag gtg gct ttg ccc ctg gtc act gtg aat cag tgc cgg cag       577
Leu Gln Gln Val Ala Leu Pro Leu Val Thr Val Asn Gln Cys Arg Gln
            145                 150                 155
```

-continued

| | | |
|---|---|---|
| tac tgg gac tca agt atc act gac tcc atg atc tgt gca ggt ggc gca<br>Tyr Trp Asp Ser Ser Ile Thr Asp Ser Met Ile Cys Ala Gly Gly Ala<br>              160                        165                      170 | 625 |

```
tac tgg gac tca agt atc act gac tcc atg atc tgt gca ggt ggc gca      625
Tyr Trp Asp Ser Ser Ile Thr Asp Ser Met Ile Cys Ala Gly Gly Ala
            160                 165                 170 ggt gcc tcc tcg tgc cag ggt gac tcc gga ggc cct ctt gtc tgc cag      673
Gly Ala Ser Ser Cys Gln Gly Asp Ser Gly Gly Pro Leu Val Cys Gln
        175                 180                 185 aag gga aac aca tgg gtg ctt att ggt att gtc tcc tgg ggc acc aaa      721
Lys Gly Asn Thr Trp Val Leu Ile Gly Ile Val Ser Trp Gly Thr Lys
    190                 195                 200 aac tgc aat gtg cgc gca cct gct gtg tat act cga gtt agc aag ttc      769
Asn Cys Asn Val Arg Ala Pro Ala Val Tyr Thr Arg Val Ser Lys Phe
205                 210                 215                 220 agc acc tgg atc aac cag gtc ata gcc tac aac tgagctcacc acaggccctc   822
Ser Thr Trp Ile Asn Gln Val Ile Ala Tyr Asn
                225                 230 cccagctcaa cccatttaaa ggacccaggc cctgtcccat catgcattca tgtctgtctt    882
cctggctcag gagaaagaag aggctgttga gggtccgact ccctacttgg acttctggca    942
cagaaggggc tgagtgactc cttgagtagc agtggctctt cctagagtag ccatgccgtg   1002
gccgggcccc ccaccctcc tccagggcaa ccccttggtc ctacagcaag aagccagaac   1062
tgttggaatg aatggcagcc ctccttggag aggcagcctg tttactgaat acagaggata   1122
cgtttacaaa aaaaaaaaaa aaaaaaa                                      1149

<210> SEQ ID NO 2
<211> LENGTH: 264
<212> TYPE: PRT
<213> ORGANISM: Homo sapiens

<400> SEQUENCE: 2

Met Leu Leu Leu Ser Leu Thr Leu Ser Leu Val Leu Leu Gly Ser Ser
            -30                 -25                 -20

Trp Gly Cys Gly Ile Pro Ala Ile Lys Pro Ala Leu Ser Phe Ser Gln
        -15                 -10                  -5

Arg Ile Val Asn Gly Glu Asn Ala Val Leu Gly Ser Trp Pro Trp Gln
 -1   1               5                  10                  15

Val Ser Leu Gln Asp Ser Ser Gly Phe His Phe Cys Gly Gly Ser Leu
                20                  25                  30

Ile Ser Gln Ser Trp Val Val Thr Ala Ala His Cys Asn Val Ser Pro
            35                  40                  45

Gly Arg His Phe Val Val Leu Gly Glu Tyr Asp Arg Ser Ser Asn Ala
        50                  55                  60

Glu Pro Leu Gln Val Leu Ser Val Ser Arg Ala Ile Thr His Pro Ser
    65                  70                  75

Trp Asn Ser Thr Thr Met Asn Asn Asp Val Thr Leu Leu Lys Leu Ala
 80                  85                  90                  95

Ser Pro Ala Gln Tyr Thr Thr Arg Ile Ser Pro Val Cys Leu Ala Ser
                100                 105                 110

Ser Asn Glu Ala Leu Thr Glu Gly Leu Thr Cys Val Thr Thr Gly Trp
            115                 120                 125

Gly Arg Leu Ser Gly Val Gly Asn Val Thr Pro Ala His Leu Gln Gln
        130                 135                 140

Val Ala Leu Pro Leu Val Thr Val Asn Gln Cys Arg Gln Tyr Trp Asp
    145                 150                 155

Ser Ser Ile Thr Asp Ser Met Ile Cys Ala Gly Gly Ala Gly Ala Ser
160                 165                 170                 175
```

-continued

```
Ser Cys Gln Gly Asp Ser Gly Pro Leu Val Cys Gln Lys Gly Asn
            180             185             190

Thr Trp Val Leu Ile Gly Ile Val Ser Trp Gly Thr Lys Asn Cys Asn
        195             200             205

Val Arg Ala Pro Ala Val Tyr Thr Arg Val Ser Lys Phe Ser Thr Trp
        210             215             220

Ile Asn Gln Val Ile Ala Tyr Asn
    225             230
```

<210> SEQ ID NO 3
<211> LENGTH: 834
<212> TYPE: DNA
<213> ORGANISM: Mus sp.
<220> FEATURE:
<221> NAME/KEY: mat_peptide
<222> LOCATION: (132)..()
<223> OTHER INFORMATION:
<220> FEATURE:
<221> NAME/KEY: CDS
<222> LOCATION: (33)..(824)
<223> OTHER INFORMATION:

<400> SEQUENCE: 3

```
gaccatctca acaccattcc ttatttgtca ca atg cta ctg ctc agc cta acc         53
                                   Met Leu Leu Leu Ser Leu Thr
                                                -30 ctt agc ctg gtc ctc ctt ggc tcc tcc tgg ggc tgt ggt gtt cct gcc        101
Leu Ser Leu Val Leu Leu Gly Ser Ser Trp Gly Cys Gly Val Pro Ala
    -25                 -20                 -15 atc acg cct gca ctg agc tac aat cag aga att gtc aac ggg gag aat        149
Ile Thr Pro Ala Leu Ser Tyr Asn Gln Arg Ile Val Asn Gly Glu Asn
-10                  -5              -1   1               5 gca gtg cca ggc tcc tgg ccc tgg cag gtg tct ctc cag gat aac acc        197
Ala Val Pro Gly Ser Trp Pro Trp Gln Val Ser Leu Gln Asp Asn Thr
                10                  15                  20 ggc ttc cac ttc tgc ggt ggt tct ctc atc agt ccg aac tgg gtg gtc        245
Gly Phe His Phe Cys Gly Gly Ser Leu Ile Ser Pro Asn Trp Val Val
            25                  30                  35 acg gct gcc cac tgc caa gtc acg cct gga cgc cac ttt gtc gtt ttg        293
Thr Ala Ala His Cys Gln Val Thr Pro Gly Arg His Phe Val Val Leu
        40                  45                  50 gga gaa tat gac cga tct tcc aat gct gaa cct gtg cag gtc ctc tcg        341
Gly Glu Tyr Asp Arg Ser Ser Asn Ala Glu Pro Val Gln Val Leu Ser
55                  60                  65                  70 atc gca agg gcc atc aca cac cct aac tgg aac gcc aac acc atg aac        389
Ile Ala Arg Ala Ile Thr His Pro Asn Trp Asn Ala Asn Thr Met Asn
                75                  80                  85 aat gac ctg act ctc ctg aag ctt gcc tcg cca gcc cgg tac aca gca        437
Asn Asp Leu Thr Leu Leu Lys Leu Ala Ser Pro Ala Arg Tyr Thr Ala
            90                  95                 100 caa gtc tca cca gtc tgc ctg gct tcc aca aac gag gca ctg cct tcg        485
Gln Val Ser Pro Val Cys Leu Ala Ser Thr Asn Glu Ala Leu Pro Ser
        105                 110                 115 ggg ctc acc tgt gtc acc act ggc tgg ggc cga atc agt ggt gtg ggc        533
Gly Leu Thr Cys Val Thr Thr Gly Trp Gly Arg Ile Ser Gly Val Gly
    120                 125                 130 aat gtg aca cca gct cgc ctg cag caa gtt gtt cta ccc ctg gtc act        581
Asn Val Thr Pro Ala Arg Leu Gln Gln Val Val Leu Pro Leu Val Thr
135                 140                 145                 150 gtg aat cag tgt cgg cag tac tgg ggt gca cgc att acc gat gcc atg        629
Val Asn Gln Cys Arg Gln Tyr Trp Gly Ala Arg Ile Thr Asp Ala Met
                155                 160                 165
```

```
ata tgt gca ggt ggc tca ggc gcc tcc tca tgt cag ggt gac tca gga        677
Ile Cys Ala Gly Gly Ser Gly Ala Ser Ser Cys Gln Gly Asp Ser Gly
        170                 175                 180 ggc cct ctt gtc tgc cag aag gga aac acc tgg gtg ctt att ggg att        725
Gly Pro Leu Val Cys Gln Lys Gly Asn Thr Trp Val Leu Ile Gly Ile
        185                 190                 195 gtc tcc tgg ggc act aag aac tgc aac ata caa gca ccg gcc atg tac        773
Val Ser Trp Gly Thr Lys Asn Cys Asn Ile Gln Ala Pro Ala Met Tyr
    200                 205                 210 act cgg gtc agc aag ttc agt acc tgg atc aac caa gtc atg gcc tac        821
Thr Arg Val Ser Lys Phe Ser Thr Trp Ile Asn Gln Val Met Ala Tyr
215                 220                 225                 230 aac taaactgtcc                                                         834
Asn

<210> SEQ ID NO 4
<211> LENGTH: 264
<212> TYPE: PRT
<213> ORGANISM: Mus sp.

<400> SEQUENCE: 4

Met Leu Leu Leu Ser Leu Thr Leu Ser Leu Val Leu Leu Gly Ser Ser
            -30                 -25                 -20

Trp Gly Cys Gly Val Pro Ala Ile Thr Pro Ala Leu Ser Tyr Asn Gln
        -15                 -10                  -5

Arg Ile Val Asn Gly Glu Asn Ala Val Pro Gly Ser Trp Pro Trp Gln
 -1  1               5                  10                  15

Val Ser Leu Gln Asp Asn Thr Gly Phe His Phe Cys Gly Gly Ser Leu
                20                  25                  30

Ile Ser Pro Asn Trp Val Val Thr Ala Ala His Cys Gln Val Thr Pro
            35                  40                  45

Gly Arg His Phe Val Val Leu Gly Glu Tyr Asp Arg Ser Ser Asn Ala
        50                  55                  60

Glu Pro Val Gln Val Leu Ser Ile Ala Arg Ala Ile Thr His Pro Asn
    65                  70                  75

Trp Asn Ala Asn Thr Met Asn Asn Asp Leu Thr Leu Leu Lys Leu Ala
80                  85                  90                  95

Ser Pro Ala Arg Tyr Thr Ala Gln Val Ser Pro Val Cys Leu Ala Ser
                100                 105                 110

Thr Asn Glu Ala Leu Pro Ser Gly Leu Thr Cys Val Thr Thr Gly Trp
            115                 120                 125

Gly Arg Ile Ser Gly Val Gly Asn Val Thr Pro Ala Arg Leu Gln Gln
        130                 135                 140

Val Val Leu Pro Leu Val Thr Val Asn Gln Cys Arg Gln Tyr Trp Gly
    145                 150                 155

Ala Arg Ile Thr Asp Ala Met Ile Cys Ala Gly Gly Ser Gly Ala Ser
160                 165                 170                 175

Ser Cys Gln Gly Asp Ser Gly Gly Pro Leu Val Cys Gln Lys Gly Asn
                180                 185                 190

Thr Trp Val Leu Ile Gly Ile Val Ser Trp Gly Thr Lys Asn Cys Asn
            195                 200                 205

Ile Gln Ala Pro Ala Met Tyr Thr Arg Val Ser Lys Phe Ser Thr Trp
        210                 215                 220

Ile Asn Gln Val Met Ala Tyr Asn
    225                 230
```

<210> SEQ ID NO 5
<211> LENGTH: 99
<212> TYPE: DNA
<213> ORGANISM: Artificial Sequence
<220> FEATURE:
<223> OTHER INFORMATION: Designed oligonucleotide to construct plasmid
    pSecTrypHis.

<400> SEQUENCE: 5
aagcttggct agcaacacca tgaatctact cctgatcctt acctttgttg ctgctgctgt    60
tgctgccccc tttgacgacg atgacaagga tccgaattc                          99

<210> SEQ ID NO 6
<211> LENGTH: 99
<212> TYPE: DNA
<213> ORGANISM: Artificial Sequence
<220> FEATURE:
<223> OTHER INFORMATION: Designed oligonucleotide to construct plasmid
    pSecTrypHis.

<400> SEQUENCE: 6
gaattcggat ccttgtcatc gtcgtcaaag ggggcagcaa cagcagcagc aacaaaggta    60
aggatcagga gtagattcat ggtgttgcta gccaagctt                          99

<210> SEQ ID NO 7
<211> LENGTH: 15
<212> TYPE: DNA
<213> ORGANISM: Artificial Sequence
<220> FEATURE:
<223> OTHER INFORMATION: Designed oligonucleotide primer to amplify
    neurosin-encoding sequence.

<400> SEQUENCE: 7
ttggtgcatg gcgga                                                    15

<210> SEQ ID NO 8
<211> LENGTH: 27
<212> TYPE: DNA
<213> ORGANISM: Artificial Sequence
<220> FEATURE:
<223> OTHER INFORMATION: Designed oligonucleotide primer to amplify
    neurosin-encoding sequence.

<400> SEQUENCE: 8
tcctcgagac ttggcctgaa tggtttt                                       27

<210> SEQ ID NO 9
<211> LENGTH: 35
<212> TYPE: DNA
<213> ORGANISM: Artificial Sequence
<220> FEATURE:
<223> OTHER INFORMATION: Designed oligonucleotide primer to amplify a
    portion of plasmid pSecTrypHis/Neurosin.

<400> SEQUENCE: 9
gcgctagcag atctccatga atctactcct gatcc                              35

<210> SEQ ID NO 10
<211> LENGTH: 29
<212> TYPE: DNA
<213> ORGANISM: Artificial Sequence
<220> FEATURE:
<223> OTHER INFORMATION: Designed oligonucleotide primer to amplify a
    portion of plasmid pSecTrypHis/Neurosin.

<400> SEQUENCE: 10

-continued

```
tgaagcttgc catggaccaa cttgtcatc                                          29
```

<210> SEQ ID NO 11
<211> LENGTH: 26
<212> TYPE: DNA
<213> ORGANISM: Artificial Sequence
<220> FEATURE:
<223> OTHER INFORMATION: Designed oligonucleotide primer to amplify a
      portion of plasmid pTrypHis.

<400> SEQUENCE: 11

```
ccaagcttca ccatcaccat caccat                                             26
```

<210> SEQ ID NO 12
<211> LENGTH: 17
<212> TYPE: DNA
<213> ORGANISM: Artificial Sequence
<220> FEATURE:
<223> OTHER INFORMATION: Designed oligonucleotide primer to amplify a
      portion of plasmid pTrySigTag.

<400> SEQUENCE: 12

```
gcacagtcga ggctgat                                                       17
```

<210> SEQ ID NO 13
<211> LENGTH: 17
<212> TYPE: DNA
<213> ORGANISM: Artificial Sequence
<220> FEATURE:
<223> OTHER INFORMATION: Designed oligonucleotide primer to amplify a
      portion of plasmid pFBTrypSigTag.

<400> SEQUENCE: 13

```
caaatgtggt atggctg                                                       17
```

<210> SEQ ID NO 14
<211> LENGTH: 20
<212> TYPE: DNA
<213> ORGANISM: Artificial Sequence
<220> FEATURE:
<223> OTHER INFORMATION: Designed oligonucleotide primer to amplify
      conserved region of serin proteases-encoding sequence.
<220> FEATURE:
<221> NAME/KEY: misc_feature
<222> LOCATION: (9)..(9)
<223> OTHER INFORMATION: n is a, c, g or t.
<220> FEATURE:
<221> NAME/KEY: misc_feature
<222> LOCATION: (12)..(12)
<223> OTHER INFORMATION: n is a, c, g or t.

<400> SEQUENCE: 14

```
gtgctcacng cngcbcaytg                                                    20
```

<210> SEQ ID NO 15
<211> LENGTH: 20
<212> TYPE: DNA
<213> ORGANISM: Artificial Sequence
<220> FEATURE:
<223> OTHER INFORMATION: Designed oligonucleotide primer to amplify
      conserved region of serin proteases-encoding sequence.
<220> FEATURE:
<221> NAME/KEY: misc_feature
<222> LOCATION: (12)..(12)
<223> OTHER INFORMATION: n is a, c, g or t.
<220> FEATURE:
<221> NAME/KEY: misc_feature
<222> LOCATION: (15)..(15)
<223> OTHER INFORMATION: n is a, c, g or t.

<400> SEQUENCE: 15
ccvctrwsdc cnccnggcga					20

<210> SEQ ID NO 16
<211> LENGTH: 20
<212> TYPE: DNA
<213> ORGANISM: Artificial Sequence
<220> FEATURE:
<223> OTHER INFORMATION: Designed oligonucleotide primer for RACE for
      hBSSP5 (forward).

<400> SEQUENCE: 16
tgtcagccct ggccgccatt					20

<210> SEQ ID NO 17
<211> LENGTH: 20
<212> TYPE: DNA
<213> ORGANISM: Artificial Sequence
<220> FEATURE:
<223> OTHER INFORMATION: Designed oligonucleotide primer for RACE for
      hBSSP5 (forward).

<400> SEQUENCE: 17
gcgagtatga ccgatcatca					20

<210> SEQ ID NO 18
<211> LENGTH: 20
<212> TYPE: DNA
<213> ORGANISM: Artificial Sequence
<220> FEATURE:
<223> OTHER INFORMATION: Designed oligonucleotide primer for RACE for
      hBSSP5 (reverse).

<400> SEQUENCE: 18
cgccacctgc acagatcatg					20

<210> SEQ ID NO 19
<211> LENGTH: 20
<212> TYPE: DNA
<213> ORGANISM: Artificial Sequence
<220> FEATURE:
<223> OTHER INFORMATION: Designed oligonucleotide primer for RACE for
      hBSSP5 (reverse).

<400> SEQUENCE: 19
gaatcagtgc cggcagtact					20

<210> SEQ ID NO 20
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP5F1 to amplify full length hBSSP5 (forward).

<400> SEQUENCE: 20
tgccacgatg ttgctgctca					20

<210> SEQ ID NO 21
<211> LENGTH: 20
<212> TYPE: DNA
<213> ORGANISM: Artificial Sequence
<220> FEATURE:
<223> OTHER INFORMATION: Designed oligonucleotide primer designated as
      hBSSP5F2 to amplify mature hBSSP5-encoding region (forward).

```
<400> SEQUENCE: 21
attgtcaacg gggagaatgc                                              20

<210> SEQ ID NO 22
<211> LENGTH: 27
<212> TYPE: DNA
<213> ORGANISM: Artificial Sequence
<220> FEATURE:
<223> OTHER INFORMATION: Designed oligonucleotide primer designated as
      hBSSP5R1/E to amplify full length hBSSP5 (reverse).

<400> SEQUENCE: 22
ggaattcggg tctttaatgg gttgagc                                      27

<210> SEQ ID NO 23
<211> LENGTH: 18
<212> TYPE: DNA
<213> ORGANISM: Artificial Sequence
<220> FEATURE:
<223> OTHER INFORMATION: Designed oligonucleotide primer designated as
      hBSSP5R4 for RT-PCR (reverse).

<400> SEQUENCE: 23
cctggcacga ggaggcac                                                18

<210> SEQ ID NO 24
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP5F1 for RACE for mBSSP5 (forward).

<400> SEQUENCE: 24
accatgaaca atgacctgac                                              20

<210> SEQ ID NO 25
<211> LENGTH: 17
<212> TYPE: DNA
<213> ORGANISM: Artificial Sequence
<220> FEATURE:
<223> OTHER INFORMATION: Designed oligonucleotide primer designated as
      mBSSP5F2 for RACE for mBSSP5 (forward)

<400> SEQUENCE: 25
gaatcagtgt cggcagt                                                 17

<210> SEQ ID NO 26
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP5F3 to amplify full length mBSSP5 (forward).

<400> SEQUENCE: 26
gaccatctca acaccattcc                                              20

<210> SEQ ID NO 27
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP5F mature to amplify mature mBSSP5-encoding region (forward).

<400> SEQUENCE: 27
```

```
<210> SEQ ID NO 28
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP5R2 for RACE for mBSSP5 (reverse).

<400> SEQUENCE: 28
atggcatcgg taatgcgtgc                                                 20

<210> SEQ ID NO 29
<211> LENGTH: 20
<212> TYPE: DNA
<213> ORGANISM: Artificial Sequence
<220> FEATURE:
<223> OTHER INFORMATION: Designed oligonucleotide primer designated as
      mBSSP5R3/E to amplify full length mBSSP5 (reverse).

<400> SEQUENCE: 29
caggtgtttc ccttctggca                                                 20

<210> SEQ ID NO 30
<211> LENGTH: 27
<212> TYPE: DNA
<213> ORGANISM: Artificial Sequence
<220> FEATURE:
<223> OTHER INFORMATION: Designed oligonucleotide primer designated as
      mBSSP5R3/E to amplify full length mBSSP5 (reverse).

<400> SEQUENCE: 30
ggaattcgga cagtttagtt gtaggcc                                         27

<210> SEQ ID NO 31
<211> LENGTH: 117
<212> TYPE: DNA
<213> ORGANISM: Artificial Sequence
<220> FEATURE:
<223> OTHER INFORMATION: Designed oligonucleotide to construct plasmid
      pTrypHis.

<400> SEQUENCE: 31
aagcttggct agcaacacca tgaatctact cctgatcctt acctttgttg ctgctgctgt     60
tgctgccccc tttcaccatc accatcacca tgacgacgat gacaaggatc cgaattc       117

<210> SEQ ID NO 32
<211> LENGTH: 117
<212> TYPE: DNA
<213> ORGANISM: Artificial Sequence
<220> FEATURE:
<223> OTHER INFORMATION: Designed oligonucleotide to construct plasmid
      pTrypHis.

<400> SEQUENCE: 32
gaattcggat ccttgtcatc gtcgtcatgg tgatggtgat ggtgaaaggg ggcagcaaca     60
gcagcagcaa caaaggtaag gatcaggagt agattcatgg tgttgctagc caagctt       117
```